(12) United States Patent
Luo et al.

(10) Patent No.: US 11,479,758 B2
(45) Date of Patent: Oct. 25, 2022

(54) METHOD OF IMPROVING METHYLTRANSFERASE ACTIVITY

(71) Applicant: DANMARKS TEKNISKE UNIVERSITET, Kongens Lyngby (DK)

(72) Inventors: Hao Luo, Kongens Lyngby (DK); Anne Sofie Laerke Hansen, Kongens Lyngby (DK)

(73) Assignee: Danmarks Tekniske Universitet, Kongens Lynby (DK)

( * ) Notice: Subject to any disclaimer, the term of this patent is extended or adjusted under 35 U.S.C. 154(b) by 0 days.

(21) Appl. No.: 16/326,974

(22) PCT Filed: Aug. 24, 2017

(86) PCT No.: PCT/EP2017/071381
§ 371 (c)(1),
(2) Date: Feb. 21, 2019

(87) PCT Pub. No.: WO2018/037098
PCT Pub. Date: Mar. 1, 2018

(65) Prior Publication Data
US 2019/0194601 A1 Jun. 27, 2019

(30) Foreign Application Priority Data

Aug. 24, 2016 (EP) .................................... 16185466
Apr. 21, 2017 (EP) .................................... 17167508

(51) Int. Cl.
*C12N 9/10* (2006.01)
*C12N 9/88* (2006.01)
(Continued)

(52) U.S. Cl.
CPC ............. *C12N 9/1007* (2013.01); *C12N 1/36* (2013.01); *C12N 9/1085* (2013.01); *C12N 9/88* (2013.01);
(Continued)

(58) Field of Classification Search
CPC ....... C12N 9/1007; C12N 9/1029; C12N 9/88
See application file for complete search history.

(56) References Cited

U.S. PATENT DOCUMENTS 7,745,195 B2 6/2010 Chateau et al.
10,316,322 B2 * 6/2019 Groff .................... C12N 15/70
(Continued)

FOREIGN PATENT DOCUMENTS

WO WO 2006/082252 8/2006
WO WO 2013/127915 9/2013
(Continued)

OTHER PUBLICATIONS

Singhal. Regulation of homocysteine metabolism by *Mycobacterium tuberculosis* S-adenosylhomocysteine hydrolase. Scientific Reports. 3:2264. pp. 1-13. 2013.*
(Continued)

*Primary Examiner* — Yong D Pak
(74) *Attorney, Agent, or Firm* — McHale & Slavin, P.A.

(57) ABSTRACT

Methods for evolving cells or strains towards improved methyltransferase activity, particularly SAM-dependent methyltransferase activity, as well as to cells and strains useful in such methods and methods of using the evolved cells in the production of methylated products.

13 Claims, 6 Drawing Sheets

Specification includes a Sequence Listing.

(51) Int. Cl.
  *C12N 1/14* (2006.01)
  *C12N 1/36* (2006.01)
  *C12N 15/10* (2006.01)
(52) U.S. Cl.
  CPC ...... *C12N 15/10* (2013.01); *C12Y 201/01004* (2013.01); *C12Y 205/01048* (2013.01); *C12Y 403/01019* (2013.01); *C12Y 404/01001* (2013.01); *C12Y 404/01021* (2013.01)

(56) References Cited

U.S. PATENT DOCUMENTS

| | | |
|---|---|---|
| 2012/0100619 A1 | 4/2012 | Nett |
| 2014/0134689 A1 | 5/2014 | Lee et al. |
| 2015/0024440 A1* | 1/2015 | Knight ........... C12Y 402/01096 435/121 |

FOREIGN PATENT DOCUMENTS

| | | | |
|---|---|---|---|
| WO | WO 2015/032911 | 3/2015 | |
| WO | WO-2016004024 A1 * | 1/2016 | ............. C12N 15/70 |

OTHER PUBLICATIONS

I7FH72, A0R2X8, and I7FZX1. UniProtKB Database, retrieved via https://www.uniprot.org/on Nov. 9, 2020.*
Hajj. Cell division, one-carbon metabolism and methionine synthesis in a metK-deficient *Escherichia coli* mutant, and a role for MmuM. Microbiology (2013), 159, 2036-2048.*
W1HI98 and W1HHI7. UniProtKB Database, retrieved via https://www.uniprot.org/on Nov. 9, 2020.*
Cherest. Cysteine Biosynthesis in *Saccharomyces cerevisiae* Occurs through the Transsulfuration Pathway Which Has Been Built Up by Enzyme RecruitmentJOURNAL of Bacteriology, Sep. 1993, p. 5366-5374.*
Duchin et al., "A continuous kinetic assay for protein and DNA methyltransferase enzymatic activities", Epigenetics and Chromatin, 2015, pp. 2-9, 8:56.
Baba et al, "Construction of *Escherichia coli* K-12 in-frame, single-gene knockout mutants: the Keio collection", Molecular Systems Biology (2006), pp. 1-11, doi:10.1038/msb4100050.
Schauder et al., "The LuxS family of bacterial autoinducers: biosynthesis of a novel quorum-sensing signal molecule", Molecular Microbiology (2001), pp. 463-476, 41 (2).
Andre et al., "Global regulation of gene expression in response to cysteine availability in *Clostridium perfringen*'s, BMC Microbiology, 2010, pp. 1-15,10:234.
Ferla et al., "Bacterial methionine biosynthesis", Microbiology (2014), pp. 1571-1584, 160.
Qiu et al., Functional analysis of serine acetyltransferase from *Mycobacterium smegmatis*, Journal of Basic Microbiology, 2014, pp. 670-677, 54.
Struck et al., "S-Adenosyl-Methionine-Dependent Methyltransferases: Highly Versatile Enzymes in Biocatalysis, Biosynthesis and Other Biotechnological Applications", Chembiochem. 2012, pp. 2642-2655, 13(18).
Neidhardt et al., "Chemical Composition of *Escherichia coli*", Chapter 3, *Escherichia coli* and *Salmonella*: cellular and molecular biology, 2nd edition, vol. 1. (1996), pp. 13-16, American Society of Microbiology Press.
Tengg et al., "Molecular characterization of the C-methyltransferase Novo of Streptomyces spheroides, a valuable enzyme for performing Friedel-Crafts alkylation", Journal of Molecular Catalysis B: Enzymatic 2012, pp. 2-8, 84.
Lyon et al., "Arylamine N Methyltransferase", The Journal of Biological Chemistry, 1982, pp. 7531-7535, vol. 257, No. 13.
Attieh et al., "Cloning and functional expression of two plant thiol methyltransferases: a new class of enzymes involved in the biosynthesis of sulfur volatiles", Plant Molecular Biology, 2002, pp. 511-521, 50.
Bennett et al., "Absolute metabolite concentrations and implied enzyme active site occupancy in *Escherichia coli*", Nature Chemical Biology, 2009, pp. 593-599, vol. 5, No. 8.
Ye et al., "A Metabolic Function for Phospholipid and Histone Methylation", Molecular Cell, 2017, pp. 1-14, 66.
Sadhu et al., "Multiple inputs control sulfur-containing amino acid synthesis in *Saccharomyces cerevisiae*", Molecular Biology of the Cell, 2014, 1653-1665, vol. 25.
McKeague et al., "Engineering amicrobial platform for de novo biosynthesis of diverse Methylxanthines", Metabolic Engineering, 2016, pp. 191-203, 38.
Gietz et al., High-efficiency yeast transformation using the LiAc/SS carrier DNA/PEG method Nature Protocols, 2007, pp. 31-34, vol. 2, No. 1.
Geu-flores et al., "USER fusion: a rapid and efficient method for simultaneous fusion and cloning of multiple PCR products", Nucleic Acids Research, 2007, pp. 1-6, vol. 35, No. 7, e555.
Verduyn et al., "Effect of Benzoic Acid on Metabolic Fluxes in Yeasts: A Continuous-Culture Study on the Regulation of Respiration and Alcoholic Fermentation", Yeast, 1992 pp. 501-517, vol. 8.
Sikorski et al., "A System of Shuttle Vectors and Yeast Host Strains Designed for Efficient Manipulation of DNA in *Saccharomyces ceretisiae*", Genetics, 1989, pp. 19-27, vol. 122, No. 1.
Jensen et al., "EasyClone: method for iterative chromosomal integration of multiple genes in *Saccharomyces cerevisiae*", FEMS Yeast Research, 2014, pp. 238-248, 14.

* cited by examiner

A

B

C

D

SEQUENCE LISTING

```
<160> NUMBER OF SEQ ID NOS: 12

<210> SEQ ID NO 1
<211> LENGTH: 394
<212> TYPE: PRT
<213> ORGANISM: Saccharomyces cerevisiae

<400> SEQUENCE: 1

Met Thr Leu Gln Glu Ser Asp Lys Phe Ala Thr Lys Ala Ile His Ala
1               5                   10                  15

Gly Glu His Val Asp Val His Gly Ser Val Ile Glu Pro Ile Ser Leu
            20                  25                  30

Ser Thr Thr Phe Lys Gln Ser Ser Pro Ala Asn Pro Ile Gly Thr Tyr
        35                  40                  45

Glu Tyr Ser Arg Ser Gln Asn Pro Asn Arg Glu Asn Leu Glu Arg Ala
    50                  55                  60

Val Ala Ala Leu Glu Asn Ala Gln Tyr Gly Leu Ala Phe Ser Ser Gly
65                  70                  75                  80

Ser Ala Thr Thr Ala Thr Ile Leu Gln Ser Leu Pro Gln Gly Ser His
                85                  90                  95
```

Ala Val Ser Ile Gly Asp Val Tyr Gly Gly Thr His Arg Tyr Phe Thr
                100                 105                 110

Lys Val Ala Asn Ala His Gly Val Glu Thr Ser Phe Thr Asn Asp Leu
            115                 120                 125

Leu Asn Asp Leu Pro Gln Leu Ile Lys Glu Asn Thr Lys Leu Val Trp
130                 135                 140

Ile Glu Thr Pro Thr Asn Pro Thr Leu Lys Val Thr Asp Ile Gln Lys
145                 150                 155                 160

Val Ala Asp Leu Ile Lys Lys His Ala Ala Gly Gln Asp Val Ile Leu
                165                 170                 175

Val Val Asp Asn Thr Phe Leu Ser Pro Tyr Ile Ser Asn Pro Leu Asn
            180                 185                 190

Phe Gly Ala Asp Ile Val Val His Ser Ala Thr Lys Tyr Ile Asn Gly
        195                 200                 205

His Ser Asp Val Val Leu Gly Val Leu Ala Thr Asn Asn Lys Pro Leu
    210                 215                 220

Tyr Glu Arg Leu Gln Phe Leu Gln Asn Ala Ile Gly Ala Ile Pro Ser
225                 230                 235                 240

Pro Phe Asp Ala Trp Leu Thr His Arg Gly Leu Lys Thr Leu His Leu
                245                 250                 255

Arg Val Arg Gln Ala Ala Leu Ser Ala Asn Lys Ile Ala Glu Phe Leu
            260                 265                 270

Ala Ala Asp Lys Glu Asn Val Val Ala Val Asn Tyr Pro Gly Leu Lys
        275                 280                 285

Thr His Pro Asn Tyr Asp Val Val Leu Lys Gln His Arg Asp Ala Leu
    290                 295                 300

Gly Gly Gly Met Ile Ser Phe Arg Ile Lys Gly Gly Ala Glu Ala Ala
305                 310                 315                 320

Ser Lys Phe Ala Ser Ser Thr Arg Leu Phe Thr Leu Ala Glu Ser Leu
                325                 330                 335

Gly Gly Ile Glu Ser Leu Leu Glu Val Pro Ala Val Met Thr His Gly
            340                 345                 350

Gly Ile Pro Lys Glu Ala Arg Glu Ala Ser Gly Val Phe Asp Asp Leu
        355                 360                 365

Val Arg Ile Ser Val Gly Ile Glu Asp Thr Asp Asp Leu Leu Glu Asp
    370                 375                 380

Ile Lys Gln Ala Leu Lys Gln Ala Thr Asn
385                 390

<210> SEQ ID NO 2
<211> LENGTH: 421
<212> TYPE: PRT
<213> ORGANISM: Corynebacterium glutamicum

<400> SEQUENCE: 2

Met Ser Asp Phe Leu Asn Ala Asp Gly Ser Leu Asn Val Asp Lys Val
1               5                   10                  15

Arg Glu Glu Phe Pro Ile Leu Lys Arg Thr Val Arg Asp Gly Lys Pro
                20                  25                  30

Leu Ala Tyr Leu Asp Ser Gly Ala Thr Ser Gln Arg Pro Glu Arg Val
            35                  40                  45

Trp Arg Ala Glu Glu His Phe Val Leu His Thr Asn Ala Pro Val His
        50                  55                  60

Arg Gly Ala Tyr Gln Leu Ala Glu Glu Ala Thr Asp Ala Tyr Glu Gly

```
                65                  70                  75                  80
Ala Arg Glu Lys Ile Ala Ala Phe Val Gly Ala Glu Gln His Glu Ile
                    85                  90                  95

Ala Phe Thr Lys Asn Ala Thr Glu Ala Leu Asn Leu Val Ala Tyr Thr
                    100                 105                 110

Leu Gly Asp Asp Arg Ser Gly Lys Tyr Arg Val Gln Ala Gly Asp Thr
                    115                 120                 125

Val Val Ile Thr Glu Leu Glu His His Ala Asn Leu Val Pro Trp Gln
            130                 135                 140

Glu Leu Cys Arg Arg Thr Gly Ala Thr Leu Lys Trp Tyr Lys Val Thr
145                 150                 155                 160

Glu Asp Gly Arg Ile Asp Leu Asp Ser Leu Glu Leu Asp Glu Thr Val
                165                 170                 175

Lys Val Val Ala Phe Thr His Gln Ser Asn Val Thr Gly Ala Val Ala
                180                 185                 190

Asp Val Pro Glu Leu Val Arg Arg Ala Lys Ala Val Gly Ala Leu Thr
            195                 200                 205

Val Leu Asp Ala Cys Gln Ser Val Pro His Met Pro Val Asn Phe His
        210                 215                 220

Glu Leu Asp Val Asp Phe Ser Ala Phe Ser Gly His Lys Met Leu Gly
225                 230                 235                 240

Pro Ala Gly Val Gly Val Val Tyr Ala Lys Ser Pro Ile Leu Asp Glu
                245                 250                 255

Leu Pro Pro Phe Leu Thr Gly Gly Ser Met Ile Glu Val Val Thr Met
                260                 265                 270

Glu Gly Ser Thr Tyr Ala Ala Ala Pro Gln Arg Phe Glu Ala Gly Thr
            275                 280                 285

Gln Met Thr Ser Gln Val Val Gly Leu Gly Ala Ala Val Asp Met Leu
            290                 295                 300

Asn Glu Ile Gly Met Glu Ala Ile Ala Ala His Glu His Ala Leu Thr
305                 310                 315                 320

Ala Tyr Ala Leu Glu Lys Leu Thr Ala Ile Lys Gly Leu Thr Ile Ala
                325                 330                 335

Gly Pro Leu Thr Ala Glu Gln Arg Gly Ala Ile Ser Phe Gly Val
                340                 345                 350

Glu Gly Ile His Pro His Asp Leu Gly Gln Val Leu Asp Asp Gln Gly
            355                 360                 365

Val Asn Ile Arg Val Gly His His Cys Ala Trp Pro Val His Arg Ser
        370                 375                 380

Met Asn Val Gln Ser Thr Ala Arg Ala Ser Phe Tyr Leu Tyr Asn Thr
385                 390                 395                 400

Phe Glu Glu Ile Asp Arg Leu Ala Ala Ala Ile Glu Lys Ala Lys Gln
                405                 410                 415

Phe Phe Gly Val Glu
            420

<210> SEQ ID NO 3
<211> LENGTH: 392
<212> TYPE: PRT
<213> ORGANISM: Streptomyces coelicolor

<400> SEQUENCE: 3

Met Ser Asp Ser Ala Thr Thr Asp Ser Ala Gly Thr Gly Gly Glu Arg
1               5                   10                  15
```

Ser Ala Ser Ala Pro Gly Asp Gly Thr Arg Ala Val Arg Ala Gly Leu
            20                  25                  30

Pro Glu Pro Val Lys His Glu Pro Thr Leu Pro Gly Pro Val Phe Ala
        35                  40                  45

Ala His Phe His Leu Pro Gly Asp Pro Thr Gly Pro Tyr Thr Tyr Gly
    50                  55                  60

Arg Asp Glu Asn Pro Thr Trp Thr Arg Leu Glu Ser Ala Ile Gly Glu
65                  70                  75                  80

Leu Glu Ala Pro Gly Glu Ala Gly Val Glu Thr Leu Val Phe Ala Ser
                85                  90                  95

Gly Met Ala Ala Ile Ser Ser Val Leu Phe Ser Gln Leu Arg Ala Gly
            100                 105                 110

Asp Thr Ala Val Leu Pro Asp Asp Gly Tyr Gln Ala Leu Pro Leu Val
            115                 120                 125

Arg Ala Gln Leu Glu Ala Tyr Gly Ile Glu Val Arg Thr Ala Pro Thr
    130                 135                 140

Gly Arg Asp Ala Gln Leu Asp Val Leu Asp Gly Ala Lys Leu Leu Trp
145                 150                 155                 160

Ile Glu Thr Pro Ser Asn Pro Gly Leu Asp Val Cys Asp Val Arg Arg
                165                 170                 175

Leu Val Glu Ala Ala His Ala Gly Gly Ala Leu Val Ala Val Asp Asn
            180                 185                 190

Thr Leu Ala Thr Pro Leu Gly Gln Arg Pro Leu Glu Leu Gly Ala Asp
            195                 200                 205

Phe Ser Val Ala Ser Gly Thr Lys Gln Leu Thr Gly His Gly Asp Val
    210                 215                 220

Leu Leu Gly Tyr Val Ala Gly Arg Asp Ala Gly Ala Met Ala Ala Val
225                 230                 235                 240

Arg Arg Trp Arg Lys Ile Val Gly Ala Ile Pro Gly Pro Met Glu Ala
                245                 250                 255

Trp Leu Ala His Arg Ser Ile Ala Thr Leu Gln Leu Arg Val Asp Arg
            260                 265                 270

Gln Asp Ser Thr Ala Leu Lys Val Ala Glu Ala Leu Arg Thr Arg Pro
    275                 280                 285

Glu Ile Thr Gly Leu Arg Tyr Pro Gly Leu Pro Asp Asp Pro Ser His
290                 295                 300

Lys Val Ala Ser Gln Gln Met Leu Arg Tyr Gly Cys Val Val Ser Phe
305                 310                 315                 320

Thr Leu Pro Ser Arg Ala Arg Ala Asp Arg Phe Leu Asp Ala Leu Arg
                325                 330                 335

Leu Val Glu Gly Ala Thr Ser Phe Gly Gly Val Arg Ser Thr Ala Glu
            340                 345                 350

Arg Arg Gly Arg Trp Gly Gly Asp Ala Val Pro Glu Gly Phe Ile Arg
    355                 360                 365

Leu Ser Val Gly Ala Glu Asp Pro Asp Leu Val Ala Asp Leu Leu
370                 375                 380

Arg Ala Leu Asp Glu Thr Thr Glu
385                 390

<210> SEQ ID NO 4
<211> LENGTH: 390
<212> TYPE: PRT
<213> ORGANISM: Streptomyces griseus

<400> SEQUENCE: 4

Met Arg Gly Thr Pro Val His His Arg Gly Ser Ser Glu Gly Ala Gly
1               5                   10                  15

Met Ser Thr Met Gly Asp Gly Thr Arg Ala Val Arg Ala Gly Leu Pro
            20                  25                  30

Glu Pro Glu Gln Phe Gly Pro Thr Leu Pro Gly Pro Val Phe Ala Ala
        35                  40                  45

His Phe His Leu Ser Gly Glu Pro Val Gly Pro Tyr Thr Tyr Gly Arg
    50                  55                  60

Glu Thr Asn Pro Thr Trp Thr His Leu Glu Arg Ala Ile Gly Glu Leu
65                  70                  75                  80

Glu Ala Pro Gly Glu Val Gly Thr Thr Val Phe Ala Ser Gly Met
                85                  90                  95

Ala Ala Ile Thr Ala Val Leu Leu Ser Gln Val Arg Ser Gly Asp Ala
            100                 105                 110

Val Val Leu Pro Asp Asp Gly Tyr Gln Ala Leu Pro Leu Val Arg Glu
        115                 120                 125

Gln Leu Glu Ala Tyr Gly Val Glu Val Arg Thr Ala Pro Thr Gly Gly
130                 135                 140

Asp Ala Gln Gln Ala Leu Leu Thr Gly Ala Lys Leu Leu Trp Ile Glu
145                 150                 155                 160

Ser Pro Ser Asn Pro Gly Leu Asp Val Cys Asp Ile Arg Arg Leu Ala
                165                 170                 175

Gly Ala Ala His Ala Ala Gly Ala Leu Val Ala Val Asp Asn Thr Leu
            180                 185                 190

Ala Thr Pro Ile Gly Gln Arg Pro Leu Glu Leu Gly Ala Asp Phe Ser
        195                 200                 205

Val Ala Ser Asp Thr Lys Gly Met Thr Gly His Gly Asp Ile Leu Leu
    210                 215                 220

Gly His Val Thr Cys Arg Asp Pro Arg Leu Thr Ala Asp Val Arg Arg
225                 230                 235                 240

Trp Arg Lys Val Val Gly Ala Ile Pro Gly Pro Met Glu Ala Trp Leu
                245                 250                 255

Ala His Arg Ser Leu Ser Thr Leu Gln Leu Arg Val Asp Arg Gln Cys
            260                 265                 270

Ala Thr Ala Leu Ala Leu Ala Glu Ala Leu Thr Glu Arg Ala Glu Val
        275                 280                 285

Thr Gly Leu Arg Tyr Pro Gly Leu Pro Thr Asp Pro Ser His Val Val
    290                 295                 300

Ala Gly Arg Gln Met Arg Phe Gly Ser Val Val Ser Phe Glu Leu
305                 310                 315                 320

Ala Asp Arg Glu Thr Ala Glu Arg Phe Leu Ser Ala Leu Arg Leu Val
                325                 330                 335

Asp Asp Ala Thr Ser Phe Gly Gly Val Arg Ser Thr Ala Glu Arg Arg
            340                 345                 350

Gly Arg Trp Gly Gly Asp Ala Val Ala Glu Gly Phe Ile Arg Phe Ser
        355                 360                 365

Val Gly Ala Glu Asp Pro Glu Asp Leu Leu Ser Asp Val Glu Gln Ala
    370                 375                 380

Leu Asn Ala Ala Val Arg
385                 390

<210> SEQ ID NO 5
<211> LENGTH: 379

<212> TYPE: PRT
<213> ORGANISM: Bacillus subtilis

<400> SEQUENCE: 5

Met Lys Lys Lys Thr Leu Met Ile His Gly Ile Thr Gly Asp Glu
1               5                   10                  15

Lys Thr Gly Ala Val Ser Val Pro Ile Tyr Gln Val Ser Thr Tyr Lys
            20                  25                  30

Gln Pro Lys Ala Gly Gln His Thr Gly Tyr Glu Tyr Ser Arg Thr Ala
            35                  40                  45

Asn Pro Thr Arg Thr Ala Leu Glu Ala Leu Val Thr Glu Leu Glu Ser
50                      55                  60

Gly Glu Ala Gly Tyr Ala Phe Ser Ser Gly Met Ala Ala Ile Thr Ala
65                  70                  75                  80

Val Met Met Leu Phe Asn Ser Gly Asp His Val Val Leu Thr Asp Asp
                85                  90                  95

Val Tyr Gly Gly Thr Tyr Arg Val Met Thr Lys Val Leu Asn Arg Leu
            100                 105                 110

Gly Ile Glu Ser Thr Phe Val Asp Thr Ser Ser Arg Glu Glu Val Glu
            115                 120                 125

Lys Ala Ile Arg Pro Asn Thr Lys Ala Ile Tyr Ile Glu Thr Pro Thr
130                 135                 140

Asn Pro Leu Leu Lys Ile Thr Asp Leu Thr Leu Met Ala Asp Ile Ala
145                 150                 155                 160

Lys Lys Ala Gly Val Leu Leu Ile Val Asp Asn Thr Phe Asn Thr Pro
                165                 170                 175

Tyr Phe Gln Gln Pro Leu Thr Leu Gly Ala Asp Ile Val Leu His Ser
            180                 185                 190

Ala Thr Lys Tyr Leu Gly Gly His Ser Asp Val Val Gly Gly Leu Val
            195                 200                 205

Val Thr Ala Ser Lys Glu Leu Gly Glu Glu Leu His Phe Val Gln Asn
210                 215                 220

Ser Thr Gly Gly Val Leu Gly Pro Gln Asp Ser Trp Leu Leu Met Arg
225                 230                 235                 240

Gly Ile Lys Thr Leu Gly Leu Arg Met Glu Ala Ile Asp Gln Asn Ala
                245                 250                 255

Arg Lys Ile Ala Ser Phe Leu Glu Asn His Pro Ala Val Gln Thr Leu
            260                 265                 270

Tyr Tyr Pro Gly Ser Ser Asn His Pro Gly His Glu Leu Ala Lys Thr
            275                 280                 285

Gln Gly Ala Gly Phe Gly Met Ile Ser Phe Asp Ile Gly Ser Glu
290                 295                 300

Glu Arg Val Asp Ala Phe Leu Gly Asn Leu Lys Leu Phe Thr Ile Ala
305                 310                 315                 320

Glu Ser Leu Gly Ala Val Glu Ser Leu Ile Ser Val Pro Ala Arg Met
                325                 330                 335

Thr His Ala Ser Ile Pro Arg Glu Arg Arg Leu Glu Leu Gly Ile Thr
            340                 345                 350

Asp Gly Leu Ile Arg Ile Ser Val Gly Ile Glu Asp Ala Glu Asp Leu
            355                 360                 365

Leu Glu Asp Ile Gly Gln Ala Leu Glu Asn Ile
370                 375

<210> SEQ ID NO 6

```
<211> LENGTH: 405
<212> TYPE: PRT
<213> ORGANISM: Homo sapiens

<400> SEQUENCE: 6

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Pro Ile Ser Leu Ser Thr Thr Phe Lys
        35                  40                  45

Gln Gly Ala Pro Gly Gln His Ser Gly Phe Glu Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Arg Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Glu Ser Leu Gly Gly Phe Glu Ser Leu Ala Glu Leu Pro Ala
            340                 345                 350

Ile Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
```

```
                385                 390                 395                 400

Ser Gly Ser His Ser
                405

<210> SEQ ID NO 7
<211> LENGTH: 507
<212> TYPE: PRT
<213> ORGANISM: Saccharomyces cerevisiae

<400> SEQUENCE: 7

Met Thr Lys Ser Glu Gln Gln Ala Asp Ser Arg His Asn Val Ile Asp
1               5                   10                  15

Leu Val Gly Asn Thr Pro Leu Ile Ala Leu Lys Lys Leu Pro Lys Ala
            20                  25                  30

Leu Gly Ile Lys Pro Gln Ile Tyr Ala Lys Leu Glu Leu Tyr Asn Pro
        35                  40                  45

Gly Gly Ser Ile Lys Asp Arg Ile Ala Lys Ser Met Val Glu Glu Ala
    50                  55                  60

Glu Ala Ser Gly Arg Ile His Pro Ser Arg Ser Thr Leu Ile Glu Pro
65                  70                  75                  80

Thr Ser Gly Asn Thr Gly Ile Gly Leu Ala Leu Ile Gly Ala Ile Lys
                85                  90                  95

Gly Tyr Arg Thr Ile Ile Thr Leu Pro Glu Lys Met Ser Asn Glu Lys
            100                 105                 110

Val Ser Val Leu Lys Ala Leu Gly Ala Glu Ile Ile Arg Thr Pro Thr
        115                 120                 125

Ala Ala Ala Trp Asp Ser Pro Glu Ser His Ile Gly Val Ala Lys Lys
    130                 135                 140

Leu Glu Lys Glu Ile Pro Gly Ala Val Ile Leu Asp Gln Tyr Asn Asn
145                 150                 155                 160

Met Met Asn Pro Glu Ala His Tyr Phe Gly Thr Gly Arg Glu Ile Gln
                165                 170                 175

Arg Gln Leu Glu Asp Leu Asn Leu Phe Asp Asn Leu Arg Ala Val Val
            180                 185                 190

Ala Gly Ala Gly Thr Gly Gly Thr Ile Ser Gly Ile Ser Lys Tyr Leu
        195                 200                 205

Lys Glu Gln Asn Asp Lys Ile Gln Ile Val Gly Ala Asp Pro Phe Gly
    210                 215                 220

Ser Ile Leu Ala Gln Pro Glu Asn Leu Asn Lys Thr Asp Ile Thr Asp
225                 230                 235                 240

Tyr Lys Val Glu Gly Ile Gly Tyr Asp Phe Val Pro Gln Val Leu Asp
                245                 250                 255

Arg Lys Leu Ile Asp Val Trp Tyr Lys Thr Asp Asp Lys Pro Ser Phe
            260                 265                 270

Lys Tyr Ala Arg Gln Leu Ile Ser Asn Glu Gly Val Leu Val Gly Gly
        275                 280                 285

Ser Ser Gly Ser Ala Phe Thr Ala Val Val Lys Tyr Cys Glu Asp His
    290                 295                 300

Pro Glu Leu Thr Glu Asp Asp Val Ile Val Ala Ile Phe Pro Asp Ser
305                 310                 315                 320

Ile Arg Ser Tyr Leu Thr Lys Phe Val Asp Asp Glu Trp Leu Lys Lys
                325                 330                 335

Asn Asn Leu Trp Asp Asp Asp Val Leu Ala Arg Phe Ser Ser Lys
            340                 345                 350
```

```
Leu Glu Ala Ser Thr Thr Lys Tyr Ala Asp Val Phe Gly Asn Ala Thr
            355                 360                 365

Val Lys Asp Leu His Leu Lys Pro Val Ser Val Lys Glu Thr Ala
    370                 375                 380

Lys Val Thr Asp Val Ile Lys Ile Leu Lys Asp Asn Gly Phe Asp Gln
385                 390                 395                 400

Leu Pro Val Leu Thr Glu Asp Gly Lys Leu Ser Gly Leu Val Thr Leu
                405                 410                 415

Ser Glu Leu Leu Arg Lys Leu Ser Ile Asn Asn Ser Asn Asp Asn
            420                 425                 430

Thr Ile Lys Gly Lys Tyr Leu Asp Phe Lys Lys Leu Asn Asn Phe Asn
            435                 440                 445

Asp Val Ser Ser Tyr Asn Glu Asn Lys Ser Gly Lys Lys Phe Ile
    450                 455                 460

Lys Phe Asp Glu Asn Ser Lys Leu Ser Asp Leu Asn Arg Phe Phe Glu
465                 470                 475                 480

Lys Asn Ser Ser Ala Val Ile Thr Asp Gly Leu Lys Pro Ile His Ile
                485                 490                 495

Val Thr Lys Met Asp Leu Leu Ser Tyr Leu Ala
            500                 505
```

<210> SEQ ID NO 8
<211> LENGTH: 461
<212> TYPE: PRT
<213> ORGANISM: Streptomyces coelicolor

<400> SEQUENCE: 8

```
Met Gln Phe His Asp Ser Met Ile Ser Leu Val Gly Asn Thr Pro Leu
1               5                   10                  15

Val Arg Leu Asn Ser Val Ser Lys Gly Ile Arg Ala Thr Val Leu Ala
            20                  25                  30

Lys Val Glu Tyr Phe Asn Pro Gly Gly Ser Val Lys Asp Arg Ile Ala
        35                  40                  45

Leu Arg Met Ile Glu Ala Ala Glu Lys Ser Gly Glu Leu Gln Pro Gly
50                  55                  60

Gly Thr Ile Val Glu Pro Thr Ser Gly Asn Thr Gly Val Gly Leu Ala
65                  70                  75                  80

Ile Val Ala Gln Gln Lys Gly Tyr Lys Cys Ile Phe Val Cys Pro Asp
                85                  90                  95

Lys Val Ser Thr Asp Lys Ile Asn Val Leu Arg Ala Tyr Gly Ala Glu
            100                 105                 110

Val Val Val Cys Pro Thr Ala Val Asp Pro Glu His Pro Asp Ser Tyr
        115                 120                 125

Tyr Asn Val Ser Asp Arg Leu Val Arg Glu Thr Pro Gly Ala Trp Lys
    130                 135                 140

Pro Asp Gln Tyr Ser Asn Pro Asn Asn Pro Leu Ser His Tyr His Ser
145                 150                 155                 160

Thr Gly Pro Glu Leu Trp Glu Gln Thr Glu Gly Lys Ile Thr His Phe
                165                 170                 175

Val Ala Gly Val Gly Thr Gly Gly Thr Ile Ser Gly Thr Gly Arg Tyr
            180                 185                 190

Leu Lys Asp Ala Ser Asp Gly Ala Val Thr Val Ile Gly Ala Asp Pro
        195                 200                 205

Glu Gly Ser Val Tyr Ser Gly Gly Ser Gly Arg Pro Tyr Leu Val Glu
    210                 215                 220
```

```
Gly Val Gly Glu Asp Phe Trp Pro Thr Ala Tyr Asp Arg Glu Val Ala
225                 230                 235                 240

Asp Glu Ile Val Ala Val Ser Asp Lys Asp Ser Phe Gln Met Thr Arg
            245                 250                 255

Arg Leu Ala Lys Glu Glu Gly Leu Leu Val Gly Gly Ser Cys Gly Met
        260                 265                 270

Ala Val Val Ala Ala Leu Glu Val Ala Ala Arg Leu Gly Glu Asp Asp
    275                 280                 285

Val Val Val Val Leu Leu Pro Asp Ser Gly Arg Gly Tyr Leu Ser Lys
290                 295                 300

Ile Phe Asn Asp Glu Trp Met Ala Asp Tyr Gly Phe Leu Glu Asp Thr
305                 310                 315                 320

Gly Pro Ser Ala Arg Val Ala Glu Val Leu Asn His Lys Glu Gly Gly
            325                 330                 335

His Ile Pro Ser Leu Val His Met His Pro Asp Glu Thr Val Gly Gln
        340                 345                 350

Ala Ile Glu Val Leu Arg Glu Tyr Gly Val Ser Gln Met Pro Ile Val
    355                 360                 365

Lys Pro Gly Ala Gly His Pro Asp Val Met Ala Ala Glu Val Val Gly
370                 375                 380

Ser Val Val Glu Arg Glu Leu Leu Asp Ala Leu Phe Ala Lys Arg Ala
385                 390                 395                 400

Ser Leu Glu Asp Pro Leu Glu Lys His Met Ser Ala Pro Leu Pro Gln
            405                 410                 415

Val Gly Ser Gly Glu Pro Val Ala Asp Leu Met Ser Val Leu Gly Gly
        420                 425                 430

Ala Asp Ala Ala Ile Val Leu Val Glu Gly Lys Pro Thr Gly Val Val
    435                 440                 445

Ser Arg Gln Asp Leu Leu Ser Phe Leu Ala Lys Val Lys
450                 455                 460

<210> SEQ ID NO 9
<211> LENGTH: 468
<212> TYPE: PRT
<213> ORGANISM: Streptomyces griseus

<400> SEQUENCE: 9

Met Gln Phe His Asp Ser Met Ile Ser Leu Val Gly Asn Thr Pro Leu
1               5                   10                  15

Val Arg Leu Arg Asn Val Thr Ala Gly Ile Gln Ala Thr Val Leu Ala
            20                  25                  30

Lys Val Glu Tyr Phe Asn Pro Gly Gly Ser Val Lys Asp Arg Ile Ala
        35                  40                  45

Leu Arg Met Ile Glu Ala Ala Glu Gln Ser Gly Glu Leu Lys Pro Gly
    50                  55                  60

Gly Thr Ile Val Glu Pro Thr Ser Gly Asn Thr Gly Val Gly Leu Ala
65                  70                  75                  80

Ile Val Ala Gln Gln Lys Gly Tyr Lys Cys Ile Phe Val Cys Pro Asp
                85                  90                  95

Lys Val Ser Thr Asp Lys Ile Asn Val Leu Arg Ala Tyr Gly Ala Glu
            100                 105                 110

Val Val Val Cys Pro Thr Ala Val Asp Pro Glu His Pro Asp Ser Tyr
        115                 120                 125

Tyr Asn Val Ser Asp Arg Leu Val Thr Glu Thr Pro Gly Ala Trp Lys
```

Pro Asp Gln Tyr Ser Asn Pro Asn Asn Pro Arg Ser His Tyr Glu Thr
145                 150                 155                 160

Thr Gly Pro Glu Leu Trp Glu Gln Thr Glu Gly Lys Ile Thr His Phe
                165                 170                 175

Val Ala Gly Val Gly Thr Gly Thr Ile Ser Gly Thr Gly Arg Tyr
            180                 185                 190

Leu Lys Glu Ile Ser Asp Gly Ala Val Gln Val Ile Gly Ala Asp Pro
                195                 200                 205

Glu Gly Ser Val Tyr Ser Gly Gly Ser Gly Arg Pro Tyr Leu Val Glu
            210                 215                 220

Gly Val Gly Glu Asp Phe Trp Pro Ser Ala Tyr Asp Arg Asn Val Thr
225                 230                 235                 240

Asp Glu Ile Val Ala Val Ser Asp Lys Asp Ser Phe Gln Met Thr Arg
                245                 250                 255

Arg Leu Ala Lys Glu Glu Gly Leu Leu Val Gly Gly Ser Cys Gly Met
                260                 265                 270

Ala Val Gly Ala Leu Glu Val Ala Lys Arg Leu Gly Pro Asp Asp
                275                 280                 285

Val Val Val Leu Leu Pro Asp Ser Gly Arg Gly Tyr Leu Ser Lys
            290                 295                 300

Ile Phe Asn Asp Glu Trp Met Ala Asp Tyr Gly Phe Leu Glu Asn Thr
305                 310                 315                 320

Gly Thr Ser Ala Asn Val Gly Ala Val Leu Asp Phe Lys Glu Gly Pro
                325                 330                 335

Met Pro Ser Leu Val His Met His Pro Glu Glu Thr Val Gly Glu Ala
                340                 345                 350

Ile Glu Val Leu Arg Glu Tyr Gly Val Ser Gln Met Pro Ile Val Lys
                355                 360                 365

Pro Gly Ala Gly His Pro Asp Val Met Ala Ala Glu Val Ile Gly Ser
            370                 375                 380

Val Val Glu Arg Gln Leu Leu Asp Ala Leu Phe Thr Gln Arg Ala Ser
385                 390                 395                 400

Leu Ser Asp Pro Leu Glu Lys His Met Ser Ala Pro Leu Pro Gln Val
                405                 410                 415

Gly Ser Gly Glu Pro Val Glu Asp Leu Met Ala Val Leu Ser Gly Thr
            420                 425                 430

Asp Gly Ala Asp Ala Ala Ile Val Leu Val Glu Gly Lys Pro Lys Gly
            435                 440                 445

Val Val Ser Arg Gln Asp Leu Leu Ala Phe Leu Ala Glu Asp Ala Gly
    450                 455                 460

Thr Ala Lys Ala
465

<210> SEQ ID NO 10
<211> LENGTH: 309
<212> TYPE: PRT
<213> ORGANISM: Clostridium acetobutylicum

<400> SEQUENCE: 10

Met Gly Lys Ile Tyr Lys Asn Leu Ile Glu Thr Ile Gly Arg Thr Pro
1               5                   10                  15

Leu Val Glu Leu Ser Asn Tyr Lys Glu Lys Asn Lys Ile Glu Gly Asn
                20                  25                  30

```
Ile Leu Gly Lys Val Glu Tyr Phe Asn Pro Ser Gly Ser Ile Lys Asp
         35                  40                  45

Arg Ile Ala Tyr Ser Met Ile Lys Asn Ala Glu Glu Gln Gly Leu Ile
 50                  55                  60

Asn Lys Asp Thr Val Ile Glu Pro Thr Ser Gly Asn Thr Gly Val
 65                  70                  75                  80

Gly Leu Ala Phe Ile Ala Ala Lys Gly Tyr Lys Leu Val Leu Thr
                 85                  90                  95

Met Pro Glu Thr Met Ser Val Glu Arg Arg Lys Leu Leu Thr Ala Tyr
                100                 105                 110

Gly Ala Glu Ile Val Leu Thr Ser Gly Val Glu Gly Met Thr Gly Ala
                115                 120                 125

Ile Lys Lys Ala Asn Glu Leu Ala Ser Glu Asn Pro Asn Ser Phe Ile
130                 135                 140

Pro Gln Gln Phe Lys Asn Pro Ser Asn Pro Ala Ile His Glu Val Thr
145                 150                 155                 160

Thr Gly Ile Glu Ile Trp Glu Asp Thr Asp Gly Lys Val Asp Ala Val
                165                 170                 175

Val Ala Gly Val Gly Thr Gly Gly Thr Ile Thr Gly Ile Ala Lys Thr
                180                 185                 190

Leu Arg Glu Lys Asn Lys Asp Ile Lys Ile Ala Val Glu Pro Ala
                195                 200                 205

Thr Ser Pro Val Leu Ser Gly Gly Lys Ala Gly Pro His Lys Ile Gln
210                 215                 220

Gly Ile Gly Ala Gly Phe Val Pro Asp Val Tyr Glu Ala Glu Leu Ile
225                 230                 235                 240

Asp Glu Ile Ile Gln Val Lys Asn Glu Asp Ala Phe Ala Ser Ala Lys
                245                 250                 255

Glu Leu Ala Arg Glu Gly Ile Leu Ala Gly Ile Ser Ser Gly Ala
                260                 265                 270

Ala Leu Phe Ala Ala Lys Glu Val Ala Ser Arg Pro Glu Phe Lys Gly
                275                 280                 285

Lys Asn Val Val Val Ile Leu Pro Asp Ser Gly Gln Arg Tyr Leu Ser
290                 295                 300

Met Ser Val Phe Asp
305

<210> SEQ ID NO 11
<211> LENGTH: 421
<212> TYPE: PRT
<213> ORGANISM: Arabidopsis thaliana

<400> SEQUENCE: 11

Met Ala Pro Val Asn Met Thr Gly Ala Val Val Ala Ala Ala Leu
 1                   5                  10                  15

Leu Met Leu Thr Ser Tyr Ser Phe Phe Phe Arg Leu Ser Glu Lys Lys
                 20                  25                  30

Lys Arg Lys Glu Lys Leu Thr Met Arg Asn Gly Leu Val Asp Ala Ile
             35                  40                  45

Gly Asn Thr Pro Leu Ile Arg Ile Asn Ser Leu Ser Glu Ala Thr Gly
 50                  55                  60

Cys Glu Ile Leu Gly Lys Cys Glu Phe Leu Asn Pro Gly Gly Ser Val
 65                  70                  75                  80

Lys Asp Arg Val Ala Val Lys Ile Ile Gln Glu Ala Leu Glu Ser Gly
                 85                  90                  95
```

```
Lys Leu Phe Pro Gly Gly Ile Val Thr Glu Gly Ser Ala Gly Ser Thr
                100                 105                 110

Ala Ile Ser Leu Ala Thr Val Ala Pro Ala Tyr Gly Cys Lys Cys His
            115                 120                 125

Val Val Ile Pro Asp Asp Ala Ala Ile Glu Lys Ser Gln Ile Ile Glu
        130                 135                 140

Ala Leu Gly Ala Ser Val Glu Arg Val Arg Pro Val Ser Ile Thr His
145                 150                 155                 160

Lys Asp His Tyr Val Asn Ile Ala Arg Arg Ala Asp Glu Ala Asn
                165                 170                 175

Glu Leu Ala Ser Lys Arg Arg Leu Gly Ser Glu Thr Asn Gly Ile His
            180                 185                 190

Gln Glu Lys Thr Asn Gly Cys Thr Val Glu Glu Val Lys Glu Pro Ser
        195                 200                 205

Leu Phe Ser Asp Ser Val Thr Gly Gly Phe Phe Ala Asp Gln Phe Glu
210                 215                 220

Asn Leu Ala Asn Tyr Arg Ala His Tyr Glu Gly Thr Gly Pro Glu Ile
225                 230                 235                 240

Trp His Gln Thr Gln Gly Asn Ile Asp Ala Phe Val Ala Ala Ala Gly
                245                 250                 255

Thr Gly Gly Thr Leu Ala Gly Val Ser Arg Phe Leu Gln Asp Lys Asn
            260                 265                 270

Glu Arg Val Lys Cys Phe Leu Ile Asp Pro Pro Gly Ser Gly Leu Tyr
        275                 280                 285

Asn Lys Val Thr Arg Gly Val Met Tyr Thr Arg Glu Glu Ala Glu Gly
                290                 295                 300

Arg Arg Leu Lys Asn Pro Phe Asp Thr Ile Thr Glu Gly Ile Gly Ile
305                 310                 315                 320

Asn Arg Leu Thr Lys Asn Phe Leu Met Ala Lys Leu Asp Gly Gly Phe
                325                 330                 335

Arg Gly Thr Asp Lys Glu Ala Val Glu Met Ser Arg Phe Leu Leu Lys
            340                 345                 350

Asn Asp Gly Leu Phe Val Gly Ser Ser Ala Met Asn Cys Val Gly
        355                 360                 365

Ala Val Arg Val Ala Gln Thr Leu Gly Pro Gly His Thr Ile Val Thr
        370                 375                 380

Ile Leu Cys Asp Ser Gly Met Arg His Leu Ser Lys Phe His Asp Pro
385                 390                 395                 400

Lys Tyr Leu Asn Leu Tyr Gly Leu Ser Pro Thr Ala Ile Gly Leu Glu
                405                 410                 415

Phe Leu Gly Ile Lys
            420

<210> SEQ ID NO 12
<211> LENGTH: 551
<212> TYPE: PRT
<213> ORGANISM: Homo sapiens

<400> SEQUENCE: 12

Met Pro Ser Glu Thr Pro Gln Ala Glu Val Gly Pro Thr Gly Cys Pro
1               5                   10                  15

His Arg Ser Gly Pro His Ser Ala Lys Gly Ser Leu Glu Lys Gly Ser
            20                  25                  30

Pro Glu Asp Lys Glu Ala Lys Glu Pro Leu Trp Ile Arg Pro Asp Ala
```

```
                35                  40                  45
Pro Ser Arg Cys Thr Trp Gln Leu Gly Arg Pro Ala Ser Glu Ser Pro
 50                  55                  60
His His His Thr Ala Pro Ala Lys Ser Pro Lys Ile Leu Pro Asp Ile
 65                  70                  75                  80
Leu Lys Lys Ile Gly Asp Thr Pro Met Val Arg Ile Asn Lys Ile Gly
                 85                  90                  95
Lys Lys Phe Gly Leu Lys Cys Glu Leu Leu Ala Lys Cys Glu Phe Phe
                100                 105                 110
Asn Ala Gly Gly Ser Val Lys Asp Arg Ile Ser Leu Arg Met Ile Glu
                115                 120                 125
Asp Ala Glu Arg Asp Gly Thr Leu Lys Pro Gly Asp Thr Ile Ile Glu
                130                 135                 140
Pro Thr Ser Gly Asn Thr Gly Ile Gly Leu Ala Leu Ala Ala Ala Val
145                 150                 155                 160
Arg Gly Tyr Arg Cys Ile Ile Val Met Pro Glu Lys Met Ser Ser Glu
                165                 170                 175
Lys Val Asp Val Leu Arg Ala Leu Gly Ala Glu Ile Val Arg Thr Pro
                180                 185                 190
Thr Asn Ala Arg Phe Asp Ser Pro Glu Ser His Val Gly Val Ala Trp
                195                 200                 205
Arg Leu Lys Asn Glu Ile Pro Asn Ser His Ile Leu Asp Gln Tyr Arg
210                 215                 220
Asn Ala Ser Asn Pro Leu Ala His Tyr Asp Thr Thr Ala Asp Glu Ile
225                 230                 235                 240
Leu Gln Gln Cys Asp Gly Lys Leu Asp Met Leu Val Ala Ser Val Gly
                245                 250                 255
Thr Gly Gly Thr Ile Thr Gly Ile Ala Arg Lys Leu Lys Glu Lys Cys
                260                 265                 270
Pro Gly Cys Arg Ile Ile Gly Val Asp Pro Glu Gly Ser Ile Leu Ala
                275                 280                 285
Glu Pro Glu Glu Leu Asn Gln Thr Glu Gln Thr Thr Tyr Glu Val Glu
                290                 295                 300
Gly Ile Gly Tyr Asp Phe Ile Pro Thr Val Leu Asp Arg Thr Val Val
305                 310                 315                 320
Asp Lys Trp Phe Lys Ser Asn Asp Glu Glu Ala Phe Thr Phe Ala Arg
                325                 330                 335
Met Leu Ile Ala Gln Glu Gly Leu Leu Cys Gly Gly Ser Ala Gly Ser
                340                 345                 350
Thr Val Ala Val Ala Val Lys Ala Ala Gln Glu Leu Gln Glu Gly Gln
                355                 360                 365
Arg Cys Val Val Ile Leu Pro Asp Ser Val Arg Asn Tyr Met Thr Lys
                370                 375                 380
Phe Leu Ser Asp Arg Trp Met Leu Gln Lys Gly Phe Leu Lys Glu Glu
385                 390                 395                 400
Asp Leu Thr Glu Lys Lys Pro Trp Trp Trp His Leu Arg Val Gln Glu
                405                 410                 415
Leu Gly Leu Ser Ala Pro Leu Thr Val Leu Pro Thr Ile Thr Cys Gly
                420                 425                 430
His Thr Ile Glu Ile Leu Arg Glu Lys Gly Phe Asp Gln Ala Pro Val
                435                 440                 445
Val Asp Glu Ala Gly Val Ile Leu Gly Met Val Thr Leu Gly Asn Met
                450                 455                 460
```

```
Leu Ser Ser Leu Leu Ala Gly Lys Val Gln Pro Ser Asp Gln Val Gly
465                 470                 475                 480

Lys Val Ile Tyr Lys Gln Phe Lys Gln Ile Arg Leu Thr Asp Thr Leu
                485                 490                 495

Gly Arg Leu Ser His Ile Leu Glu Met Asp His Phe Ala Leu Val Val
            500                 505                 510

His Glu Gln Ile Gln Tyr His Ser Thr Gly Lys Ser Ser Gln Arg Gln
            515                 520                 525

Met Val Phe Gly Val Val Thr Ala Ile Asp Leu Leu Asn Phe Val Ala
        530                 535                 540

Ala Gln Glu Arg Asp Gln Lys
545                 550
```

METHOD OF IMPROVING METHYLTRANSFERASE ACTIVITY

FIELD OF THE INVENTION

The present invention relates to methods for evolving cells or strains towards improved methyltransferase activity as well as to the background host cells and strains useful in such methods and evolved cells or strains obtainable or obtained using such methods.

BACKGROUND OF THE INVENTION

Methyltransferases are an important group of enzymes which facilitate methylation events between methyl donors and acceptors. They can generally be divided into three classes, of which the most common one is that of S-adenosyl methionine- (SAM-) dependent methyltransferases, i.e., methyltransferases requiring the SAM molecule as a methyl donor, resulting in its conversion to S-adenosyl-L-homocysteine (SAH). The SAM-dependent methyltransferases are widely used for secondary metabolite synthesis, for example, in the biosynthesis of flavonoids in plants, neurotransmitters in animals and antibiotics in bacteria. Metabolic engineering of organisms incorporating small-molecule SAM-dependent methyltransferases can be useful for a variety of applications ranging from industrial bioprocessing of flavourants and antibiotics to frontier research in biofuel production and bioremediation (Struck et al., 2012).

One application of particular interest is the biosynthesis of melatonin. In animals, melatonin is biosynthesized from the native metabolite L-tryptophan via the intermediates 5-hydroxy-L-tryptophan (5HTP), serotonin and N-acetylserotonin. The last step is this pathway, the conversion of N-acetylserotonin and SAM to melatonin and SAH, is catalyzed by acetylserotonin O-methyltransferase (ASMT). The SAH can then be converted back to SAM via a SAM cycle, an enzymatic pathway existing in all known organisms. Recombinant production of melatonin has been described, e.g., in WO 2013/127915 A1, WO 2015/032911 A1 and US 2014/134689 AA.

Duchin et al. (2015) describes an in vitro assay for measuring methyltransferases catalyzing SAM-dependent methylation of proteins and DNA based on the coupling of SAH formation to NADP(H) oxidation through a 3-enzyme reaction including glutamate dehydrogenase.

Ye et al. (2017) describes that next to the enzyme activities of the CHO2 and OPI3 genes, the histone methyltransferases encoded by DOT1, SET1 and SET2 are major native SAM sink enzymes in yeast. Sadhu et al. (2014) describes yeast strains having deletions of MET17 (a.k.a. MET15) and CHO2.

U.S. Pat. No. 7,745,195 describes methods to evolve microorganisms under selection pressure, e.g., to improve methionine synthesis, using a background strain auxotrophic for methionine.

WO 2006/082252 A2 describes a method for the enzymatic production of alpha-ketobutyrate and its derivatives via activated homoserine.

There is still a need for improved SAM-dependent methyltransferase activity for biosynthetic applications, e.g., by improving the SAM-dependent methyltransferase itself and/or the cells in which the reaction takes place.

SUMMARY OF THE INVENTION

It has been found by the present inventor that an in vivo growth selection system can be used to improve SAM-dependent methyltransferase activity under selection pressure. The selection system utilizes background host cells which are genetically engineered to make the SAM cycle substantially the only source of homocysteine, with homocysteine being the precursor of one or more of cysteine, 2-oxobutanoate and isoleucine. The selection may then take place in the presence of methionine.

So, in one aspect, the present invention relates to a genetically modified cell which comprises
 (a) a SAM-dependent methyltransferase;
 (b) a biosynthetic pathway converting SAH to a metabolite via a homocysteine intermediate, wherein the metabolite is selected from cysteine, 2-oxobutanoate, isoleucine, or a combination of any thereof;
 (c) one or more genetic modifications disrupting any endogenous $H_2S$-dependent and/or L-cysteine-dependent biosynthesis of homocysteine in the cell,
 wherein the growth of the cell is dependent on the production of the metabolite from the biosynthetic pathway in (b).

In one aspect, the present invention relates to a genetically modified cell which comprises
 (a) a SAM-dependent methyltransferase;
 (b) a biosynthetic pathway converting SAH to cysteine via a homocysteine intermediate; and
 (c) one or more genetic modifications reducing any endogenous $H_2S$-dependent and/or L-cysteine-dependent biosynthesis of homocysteine in the cell,
wherein the growth of the cell is dependent on the production of cysteine from the biosynthetic pathway in (b).

In one aspect, the invention relates to a genetically modified cell which comprises
 (a) a SAM-dependent methyltransferase;
 (b) a biosynthetic pathway converting SAH to isoleucine via a homocysteine intermediate; and
 (c) one or more genetic modifications reducing any endogenous $H_2S$-dependent and/or L-cysteine-dependent biosynthesis of homocysteine in the cell,
wherein the growth of the cell of the cell is dependent on the production of isoleucine from the biosynthetic pathway in (b).

In one aspect, the invention relates to a genetically modified cell which comprises
 (a) a SAM-dependent methyltransferase;
 (b) a biosynthetic pathway converting SAH to 2-oxobutanoate via a homocysteine intermediate; and
 (c) one or more genetic modifications reducing any endogenous $H_2S$-dependent and/or L-cysteine-dependent biosynthesis of homocysteine in the cell,
wherein the growth of the cell of the cell is dependent on the production of 2-oxobutanoate from the biosynthetic pathway in (b).

In a specific embodiment of any aspect herein, the SAM-dependent methyltransferase is expressed from a transgene, e.g., from a heterologous gene.

In one aspect, the invention relates to a genetically modified bacterial cell comprising a SAM-dependent methyltransferase, a heterologous cystathionine-beta-synthase, a heterologous cystathionine-gamma-lyase, and
 (a) a downregulation or deletion of cysE;
 (b) a downregulation or deletion of cysK and cysM;
 (c) a downregulation or deletion of cysE and ilvA;
 (d) a downregulation or deletion of cysE and tdcB;
 (e) a downregulation or deletion of cysE, ilvA and tdcB;
 (f) a downregulation or deletion of cysE, ilvA, tdcB, and metA;

(g) a downregulation or deletion of cysE, ilvA, tdcB, and metB;

(h) a downregulation or deletion of metA, ilvA and tdcB;

(i) a downregulation or deletion of metB, ilvA and tdcB;

(j) a downregulation or deletion of metC, malY, ilvA and tdcB;

(k) a downregulation or deletion of metC, malY, ilvA, tdcB and metA;

(l) a downregulation or deletion of metC, malY, ilvA, tdcB and metB; or (m) any one of (a) to (l), further comprising a downregulation or deletion of cfa.

In one aspect, the invention relates to a genetically modified cell which is, or is derived from, an *Escherichia* cell and comprising a SAM-dependent methyltransferase, a heterologous cystathionine-beta-synthase, a heterologous cystathionine-gamma-lyase, and a downregulation or deletion of cysE and, optionally, cfa.

In one aspect, the invention relates to a genetically modified yeast cell comprising a SAM-dependent methyltransferase, optionally heterologous, and a downregulation or deletion of an endogenous gene encoding an acetylhomoserine sulfhydrylase, optionally MET17, a homoserine O-acetyltransferase, optionally MET2, a downregulation or deletion of an endogenous gene encoding a L-threonine/L-serine ammonia-lyase, optionally one or both of CHA1 and ILV1, optionally wherein the cell further comprises a downregulation or deletion of one or more of MET6, ERG6, CHO2, OPI3, SET2, SET1 and DOT1.

In one aspect, the invention relates to a genetically modified *Saccharomyces* cell comprising a SAM-dependent methyltransferase which is heterologous or overexpressed as compared to the native *Saccharomyces* cell, and (a) a downregulation or deletion of MET17;

(b) a downregulation or deletion of MET2;

(c) a downregulation or deletion of MET2 and MET17

(d) a downregulation or deletion of MET17, CHA1 and ILV1;

(e) a downregulation or deletion of MET2, CHA1 and ILV1;

(f) a downregulation or deletion of MET17, MET2, CHA1 and ILV1; or (g) any one of (a) to (f), further comprising a downregulation or deletion of MET6, or (h) any one of (a) to (g), further comprising a downregulation or deletion of one or more native SAM-dependent methyltransferases, optionally selected from one or more of ERG6, CHO2, OPI3, SET2, SET1 and DOT1.

In one aspect, the invention relates to a genetically modified cell which is, or is derived from, a *Saccharomyces* cell and comprises a SAM-dependent methyltransferase expressed from a transgene and a downregulation or deletion of MET17 and/or MET2, optionally MET6 and, optionally, one or more of ERG6, CHO2, OPI3, SET2, SET1 and DOT1.

In one aspect, the invention relates to a composition comprising a plurality of the genetically modified cell according to the invention, optionally wherein the composition comprises a culture medium comprising methionine, at least one substrate or substrate precursor of the SAM-dependent methyltransferase, and a carbon source.

In one aspect, the invention relates to a method of evolving the SAM-dependent methyltransferase activity of a cell, comprising cultivating the genetically modified cell of any aspect or embodiment herein in a medium comprising an abundance of methionine, at least one substrate or substrate precursor of the SAM-dependent methyltransferase, and a carbon source.

In one aspect, the invention relates to a method of preparing a cell having an improved SAM-dependent methyltransferase activity, comprising the steps of:

(a) culturing a plurality of the genetically modified cell of any aspect or embodiment herein in a medium comprising an abundance of methionine, at least one substrate or substrate precursor of the SAM-dependent methyltransferase, and a carbon source; and (b) selecting any cell having an increased growth rate as compared to the genetically modified cell or the composition prior to step (a) as a cell having an improved SAM-dependent methyltransferase activity.

In one aspect, the invention relates to a method of producing a cell having an improved SAM-dependent methyltransferase activity, comprising the steps of:

(a) generating a plurality of the genetically modified cell according to any aspect or embodiment herein;

(b) culturing the plurality of genetically modified cells in a medium comprising an abundance of methionine; and at least one substrate or substrate precursor of the SAM-dependent methyltransferase;

(c) selecting any cell having an increased growth rate as a cell having an improved SAM-dependent methyltransferase activity; and optionally, reversing the one or more genetic modifications in the cell.

In one aspect, the invention relates to a method of preparing a genetically modified microbial cell which is growth-dependent on a metabolite selected from cysteine, 2-oxobutanoate and isoleucine, or a combination of any thereof, comprising the steps of (a) transforming a microbial cell with a nucleic acid encoding a SAM-dependent methyltransferase;

(b) optionally, transforming the cell with nucleic acids encoding cystathionine-beta-synthase and a cystathionine-gamma-lyase;

(c) reducing or disrupting the expression or activity of at least one enzyme in any endogenous pathway for $H_2S$-dependent and/or L-cysteine-dependent biosynthesis of homocysteine in the cell, and (d) reducing or disrupting the expression or activity of at least one enzyme in any endogenous pathway for cysteine, 2-oxobutanoate or isoleucine, or a combination of any thereof;

wherein steps (a) to (d) are performed in any order. Optionally, the enzyme reduced or disrupted in (c) and (d) is the same enzyme.

In one aspect, the invention relates to a method of preparing a genetically modified microbial cell which is growth-dependent on cysteine, isoleucine or both, comprising the steps of (a) transforming a microbial cell with a nucleic acid encoding a SAM-dependent methyltransferase;

(b) optionally, transforming the cell with nucleic acids encoding cystathionine-beta-synthase and a cystathionine-gamma-lyase;

(c) reducing or disrupting the expression or activity of at least one enzyme in any endogenous pathway for $H_2S$-dependent and/or L-cysteine-dependent biosynthesis of homocysteine in the cell, wherein steps (a) to (c) are performed in any order.

In one aspect, the invention relates to a method of producing a methylated product from a substrate of a SAM-dependent methyltransferase, the method comprising the steps of:
  (a) culturing a plurality of the genetically modified cell of any aspect or embodiment herein in a medium comprising an abundance of methionine, at least one substrate or substrate precursor of the SAM-dependent methyltransferase, and a carbon source;
  (b) selecting any cell having an increased growth rate as compared to the genetically modified cell or composition prior to step (a) as a cell having an improved SAM-dependent methyltransferase activity;
  (c) producing the methylated product by fermenting a cell selected in step (b) in a medium comprising methionine, the substrate or substrate precursor of the SAM-dependent methyltransferase, and a carbon source; and
  (d) optionally, retrieving the methylated product from the cell or fermentation medium.

In one aspect, the invention relates to a cell, such as an evolved cell, produced or identified by a method according to any aspect or embodiment described herein.

These and other aspects and embodiments are described in more detail below.

DETAILED DISCLOSURE OF THE INVENTION

According to the invention, the growth or growth rate of a host cell, herein referred to as a "background" host cell, can be made dependent on efficient SAM-dependent methyltransferase activity resulting in the conversion of SAM to SAH, which in turn allows for the selection of cells where this activity has been evolved, herein referred to as "evolved" cells, under selected conditions. These can typically be identified by an improved growth over the non-evolved cell. The evolved cell can then itself be used for biosynthetic purposes, optionally reversing one or more of the genetic modifications made to enable the selection. Additionally, the genomic and/or proteomic changes or mutations that occurred in the evolved cell can be identified by well-known analytical methods, and then transferred into another cell of choice, typically of the same or a similar genus, species or strain. Such changes may, for example, occur in the SAM-dependent methyltransferase itself or in one or more native metabolic pathways in the cell.

Figure 1:
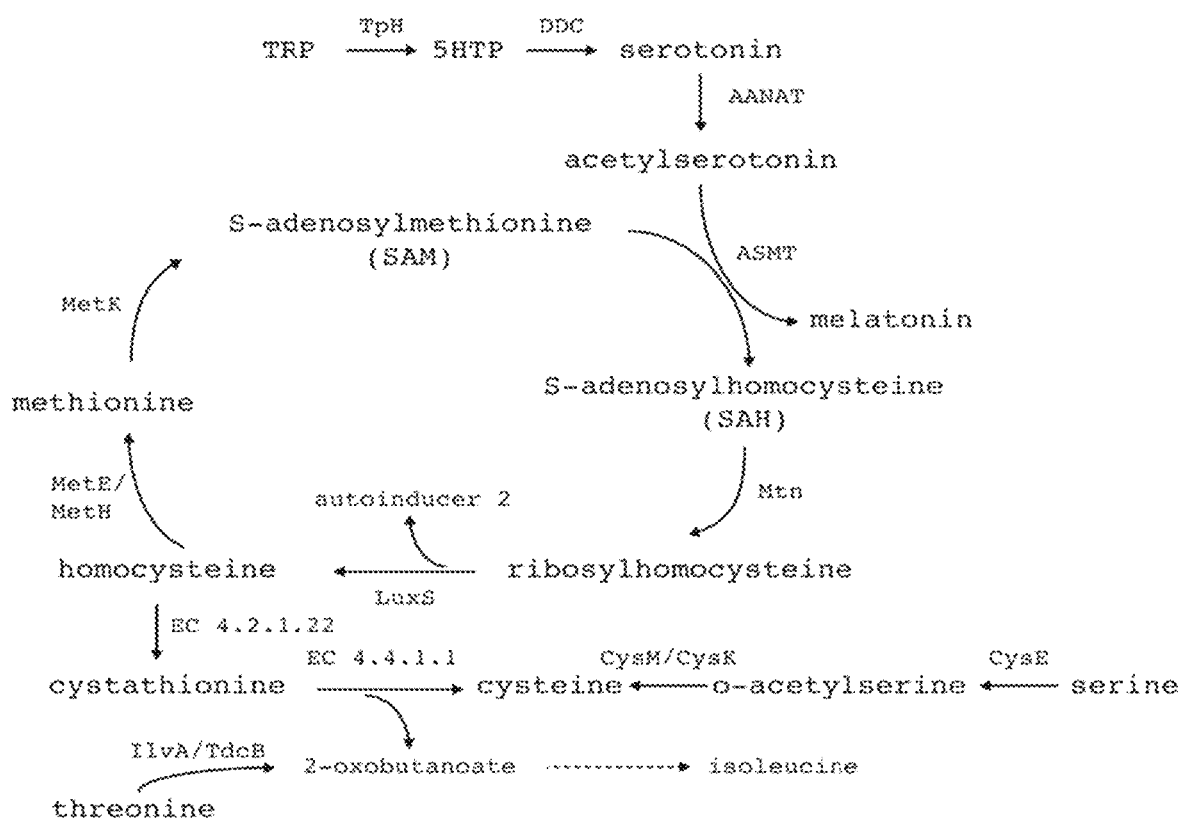
FIG. 1: Illustration of the SAM selection system using a melatonin biosynthesis pathway in E. coli. The melatonin pathway genes, encoding the enzymes TpH, DDC, AANAT and ASMT, are heterologous to E. coli. MetK, MetE, MetH, LuxS and Mtn are native E. coli proteins involved in the SAM cycle. The cystathionine-beta-synthase (EC 4.2.1.22) and cystathionine-gamma-lyase (EC 4.4.1.1) are heterologous to E. coli. In E. coli, cysteine biosynthesis is dependent on CysE. The 2-oxobutanoate is a precursor to isoleucine biosynthesis and is produced by IlvA or TdcB from threonine.

The Examples report the production of a SAM-selection background cell of the E. coli species, establishing the biosynthetic pathway converting SAH to cysteine or 2-oxobutanoate/isoleucine shown in FIG. 1. However, as described herein, the SAM selection system according to the present invention is applicable to any type of cells. For example, Example 4 describes the construction and testing of suitable S. cerevisiae background host cells, confirming that the introduced SAM-dependent methyltransferase provides a growth advantage. To enable the selection, de novo homocysteine biosynthesis is reduced, disrupted or eliminated so that homocysteine is only produced via SAM-dependent methylation events and a growth dependency on cysteine, 2-oxobutanoate and/or isoleucine is established.

Figure 2:
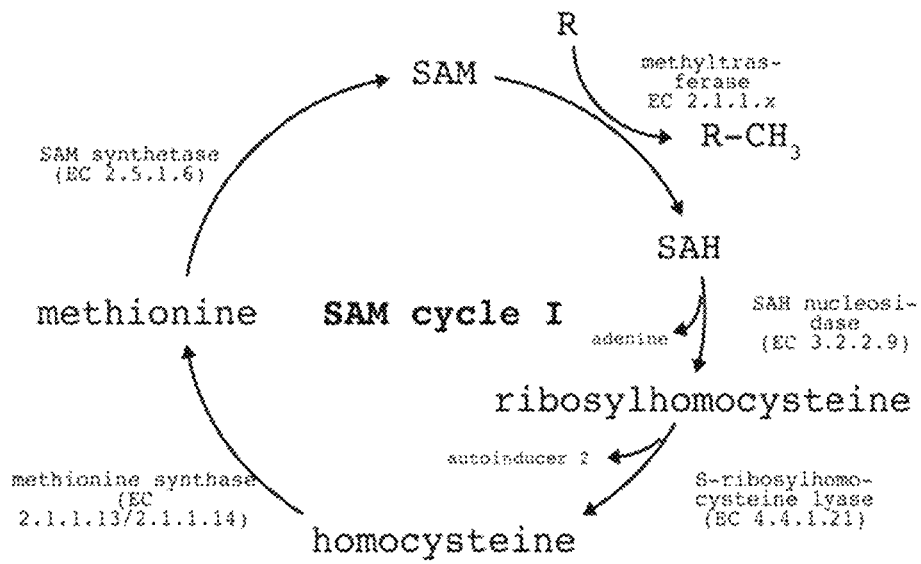
FIG. 2: Natural SAM cycles. The formation of homocysteine is a two-step enzymatic conversion in SAM cycle I (A) while it requires only a single step in SAM cycle II (B). Most organisms operate with either cycle. E. coli operates with SAM cycle I while S. cerevisiae operates with SAM cycle II.
Figure 2:
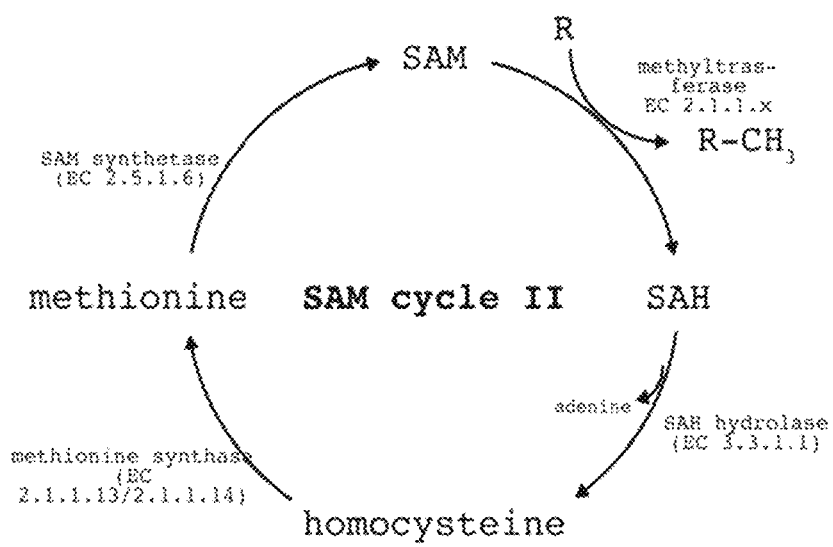

As shown in FIG. 2, two SAM cycles, I and II, exist in nature and are used by different organisms (e.g., E. coli and S. cerevisiae). The SAH to homocysteine conversion is a part of both SAM cycles. The difference between SAM cycle I and cycle II is the number enzymatic steps required for SAH to homocysteine conversion. E. coli utilize SAM cycle I and transformation of SAH to homocysteine is taken place by SAH nucleosidase and S-ribosylhomocysteine lyase encoded by mtn and luxS, respectively. S. cerevisiae employ SAM cycle II and this conversion is a single step via SAH hydrolase encoded by SAH1.

Figure 3:
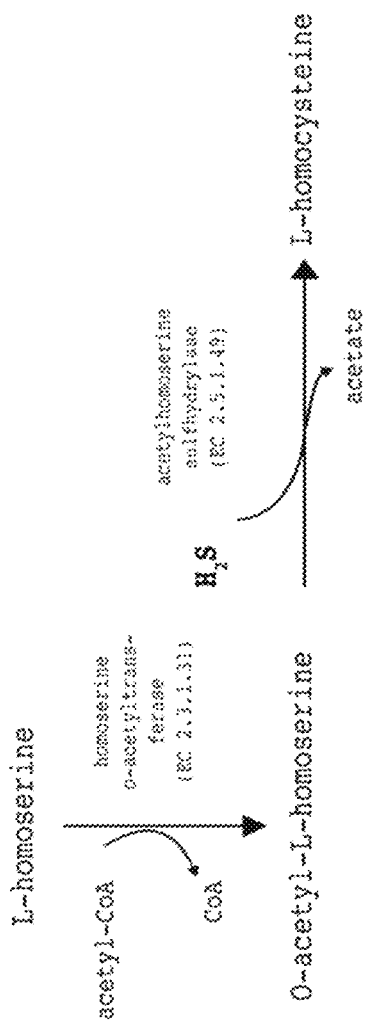
FIG. 3: Illustration of homocysteine biosynthesis pathways either via hydrogen sulfide (A) or cysteine (B).
Figure 3:
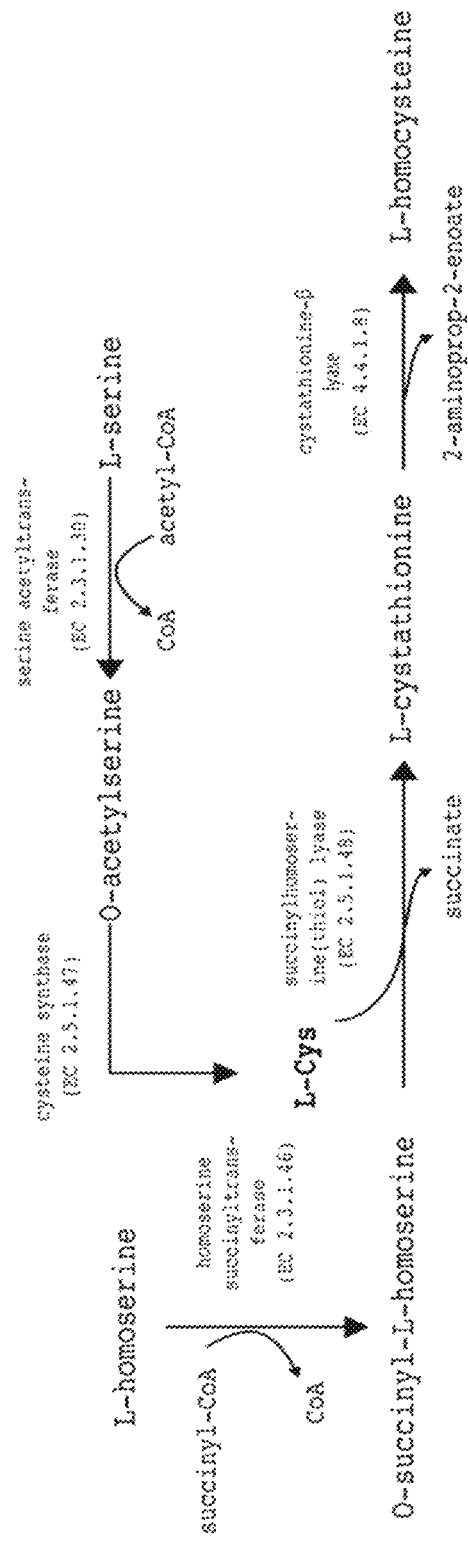

As shown in FIG. 3, homocysteine can be de novo synthesized via two pathways depending on the sulphur source(s). The sulphur source can be either hydrogen sulphite ($H_2S$) or L-cysteine. The majority of organisms shown in Table 1 contain both pathways endogenously while certain microorganisms, for example, E. coli and S. cerevisiae only contain one pathway. As selected examples, the general strategy for preventing homocysteine biosynthesis (by another route than the SAM-cycle) and coupling growth selection to cysteine, 2-oxobutanoate/isoleucine or both is presented in Table 1 for some non-limiting examples of organisms. Other choices of reaction knockouts are possible, however, as similar effects can be achieved by removing any other related reaction nodes shown in FIG. 3. For example, preventing homocysteine biosynthesis from L-cys can also be effectively achieved by deleting cystathionine-beta-lyase (EC 4.4.1.8) instead of serine acetyltransferase (EC 2.3.1.30). Since these organisms are well-known and characterized, standard biotechnology techniques can be used to remove the relevant enzyme activity, e.g., by downregulating or deleting the endogenous gene(s) encoding the enzyme(s).

Another feature of the SAM selection system is that the cell has the ability to convert homocysteine to cysteine or 2-oxobutanoate, the latter of which being a precursor of isoleucine biosynthesis. This conversion can be catalyzed by, for example, cystathionine-beta-synthase and cystathionine-gamma-lyase. As shown in Table 2, many organisms carry the encoding genes naturally. Thus, the reaction knockouts listed in Table 1 is the only requirement to establish the selection system. For example, it only requires the deletion/inactivation of one or more of acetylserine/acetylhomoserine sulfhydrylase (MET17), homoserine O-acetyltransferase (MET2) and homocysteine methyltransferase (MET6) genes to enable the SAM selection with cysteine growth coupling in S. cerevisiae. Deletion of MET6 might be advantageous to prevent direct homocysteine synthesis from methionine. The Met6 enzyme catalyses the conversion of homocysteine and methionine, but the reversibility of the reaction may depend on the conditions.

In addition, the SAM-selection system comprises functional expression of a SAM-dependent methyltransferase, optionally from a transgene, converting SAM to SAH in the methylation reaction. The methyltransferase can be expressed from any type of nucleic acid, e.g., a plasmid, an expression vector, a chromosome or other form of nucleic acid.

TABLE 1

Examples of genes to downregulate or delete, e.g., knockout, in initial host cell for the purpose of preventing de novo homocysteine biosynthesis and coupling growth selection to cysteine, 2-oxobutanoate, isoleucine or a combination thereof in various species. All reactions are described in their EC number. There may be multiple genes to carry out the same reaction. Examples of genes encoding to the corresponding enzymes are indicated within parentheses. "Other" includes, e.g., native SAM sinks.

| Species [SAM cycle] | Homocysteine biosynthesis $H_2S$-dependent | L-Cys-dependent | Cysteine selection coupling | 2-Oxo-butanoate/ Isoleucine selection coupling | Other |
|---|---|---|---|---|---|
| E. coli [I] | n.a. | EC 2.3.1.30 (cysE) EC 2.5.1.47$^a$ (cysK, cysM) EC 2.3.1.46$^a$ (metA) EC 2.5.1.48$^a$ (metB) EC 4.4.1.8$^a$ (metC, malY) | EC 2.3.1.30 (cysE) EC 2.5.1.47$^a$ (cysK, cysM) | EC 4.3.1.19 (ilvA, tdcB) EC 2.3.1.46$^b$ (metA) EC 4.3.1.-$^b$ (metB) | EC 2.1.1.79 (cfa) |
| S. cerevisiae [II] | EC 2.5.1.49 (MET17) EC 2.3.1.31$^a$ (MET2) | n.a. | EC 2.5.1.49 (MET17) EC 2.3.1.31$^a$ (MET2) | EC 4.3.1.19 (CHA1, ILV1) | EC 2.1.1.14 (MET6), EC 2.1.1.41 (ERG6), EC 2.1.1.17 (CHO2), EC 2.1.1.71 (OPI3) EC 2.1.1.43 (SET1, SET2, DOT1) |
| B. subtilis [I] | EC 2.5.1.49 (metI) | EC 2.3.1.30 (cysE) | EC 2.3.1.30 (cysE) | EC 4.3.1.19 (ilvA) | |
| C. glutamicum [I and II] | EC 2.5.1.49 (metY) | EC 2.3.1.30 (cysE) | EC 2.3.1.30 (cysE) | EC 4.3.1.19 (ilvA, tdcB) | EC 2.1.1.79 (cma) |
| S. coelicolor [II] | n.a. | EC 2.3.1.30 | EC 2.3.1.30 | EC 4.3.1.19 (SCO4962, SCO7292, SCO0821) | |
| S. griseus [II] | EC 2.5.1.49 (SGR_6647) | EC 2.3.1.30 (metX) | EC 2.3.1.30 (metX) | EC 4.3.1.19 (SGR_2048, SGR_2568) | |
| R. eutropha [I] | EC 2.5.1.49 (metY1, metY2) | EC 2.3.1.30 (cysE) | EC 2.3.1.30 (cysE) | EC 4.3.1.19 (H16_B0620, tdcB, H16_A0427), EC 1.2.7.1 (H16_B1980, H16_A1255) | |
| C. acetobutylicum [I] | EC 2.5.1.49 (CA_C0102, cysD) | EC 2.3.1.30 (cysE) | EC 2.3.1.30 (cysE) | EC 4.3.1.19 EC 1.2.7.1 | |
| A. thaliana [II] | | EC 2.5.1.47 (oasA1, oasB, AT3G61440.1) | EC 2.5.1.47 (oasA1, oasB) | EC 4.3.1.19 (AT3G10050.1) | | n.a.: not available
$^a$alternative or supplementary to first-mentioned gene(s)
$^b$enhanced selection gene(s)

TABLE 2

Examples of cystathionine-gamma-lyase (EC 4.4.1.1) and cystathionine-beta-synthase (EC 4.2.1.22) activity in preferred species

| Species | EC 4.4.1.1 coding gene | EC 4.2.1.22 coding gene | Heterologous expression preferred |
|---|---|---|---|
| E. coli[a] | n.a. | n.a. | Yes |
| S. cerevisiae[b] | CYS3 | CYS4 | No |
| B. subtilis[c] | mccB | n.i. | Yes (of EC 4.2.1.22) |
| C. glutamicum[d] | Cgl2786 | Cgl2136 | No |
| S. coelicolor[e] | SCO3920 | SCO3077 | No |
| S. griseus[f] | SGR_3660 | SGR_2592, SGR_3242, SGR_4452, SGR_4632, SGR_6231 | No |
| R. eutropha[g] | n.a. | n.a. | Yes |
| C. acetobutylicum[h] | n.a. | CA_C0931, cysK | Yes |
| A. thaliana[i] | AT5G28030.1 | AT1G55880.1 | Yes (of EC 4.4.1.1) | n.a.: not available;
n.i.: not identified;
[a] E. coli MG1655;
[b] S. cerevisiae S288C;
[c] B. subtilis 168;
[d] C. glutamicum ATCC 13032;
[e] S. coelicolor A3(2);
[f] S. griseus NBRC 13350;
[g] R. eutropha H16;
[h] C. acetobutylicum ATCC 824 and
[i] A. thaliana col As illustrated in Table 1, the SAM selection system can be established in different organisms. The genetic modifications to be introduced depend on the sulphur-donor for homocysteine biosynthesis (i.e. hydrogen sulphite or L-Cysteine, FIG. 3). In the case of S. cerevisiae, for example, deletion of the MET17 and/or MET2 gene(s) is sufficient to prevent hydrogen sulphite-dependent L-homocysteine biosynthesis. Furthermore, since L-Cysteine biosynthesis only takes place via the native cystathionine-beta-synthase and cystathionine-gamma-lyase enzymes from homocysteine, this automatically results in an L-Cysteine auxotroph upon MET17 and/or MET2 deletion and enables L-Cysteine coupled growth selection. Moreover, as already indicated above, deletion of MET6 can be beneficial since it may, under certain conditions, catalyse reversible methionine-homocysteine conversion, reducing or short-circuiting the methylation-dependent homocysteine biosynthesis.

A similar principle can be applied to A. thaliana col plant to achieve L-Cysteine coupled selection. For example, removal of EC 2.5.1.47 via inactivation of the oasA1, oasB, and AT3G61440.1 genes results not only in preventing L-homocysteine but also L-cysteine biosynthesis. However, although a native cystathionine-beta-synthase (AT1G55880.1) exists, for the purpose of improving L-Cysteine synthesis, it is preferred that cystathionine-beta-synthase and cystathionine-gamma-lyase are expressed from transgenes, transiently or otherwise.

It is also worth noting that the effectiveness of the SAM selection system can be influenced by native SAM- or methylation-sinks, i.e., native SAM-dependent methyltransferases such as Cfa in E. coli. Examples of SAM-sinks include, for example, membrane lipid methyltransferases such as Cfa of E. coli, and ERG6, CHO2, OPI3, SET2, SET1 and DOT1 of S. cerevisiae. The cfa gene in E. coli is involved in cyclopropane fatty acid biosynthesis and ERG6 is involved in ergosterol synthesis in yeast cells while CHO2 and OPI3 are part of the phospholipid phosphatidylethanolamine biosynthetic pathway. SET2, SET1 and DOT1 are involved in histone methylation in S. cerevisiae. Although the gene encoding a specific SAM sink may vary between organisms, a SAM sink can be easily determined by growth-adapting cells (prior to transforming the cells with a transgene expressing a methyltransferase of interest), followed by whole genome sequencing or transcriptome profiling for identification. See, e.g., Example 1. Alternatively, SAM sinks can be identified by knocking-down or -out selected methyltransferases in a background host cell and testing for growth in the presence of methionine (see, e.g., Example 4).

Predictability is a unique character of the SAM system according to the present invention. Using E. coli, for example, since the described SAM selection system is growth-coupled to cysteine formation and it is known there is about 87 µmol of cysteine per gram of dried cells according to Frederick et al. (1996), and since the molar ratio of intended methylation product formed (i.e., melatonin) and cysteine produced will be 1 to 1 (FIG. 1), one can easily deduce that the minimum amount of methylation required would be 87 µmol per gram of dried cells. A similar principle applies if growth selection is coupled to 2-oxobutanoate, which in turn leads to isoleucine biosynthesis. In case of E. coli growth, one can expect a further 3-fold increase in methylation activity, i.e., turnover, to a minimum amount of about 276 µmol per gram of dried cells (FIG. 1).

Definitions

The term "host cell" refers to any cell into which an exogenous nucleic acid sequence can be introduced and expressed, typically via an expression vector. The host cell may, for example, be a wild-type cell isolated from its natural environment, a mutant cell identified by screening, a cell of a commercially available strain, or a genetically engineered cell or mutant cell, comprising one or more other exogenous and/or heterologous nucleic acid sequences than those of the invention. As used herein, the term "host cell" may refer to an individual host cell or, unless contradicted by context, to a strain or clone comprising a plurality of such host cells or the host cell species as such.

A "recombinant" cell or host cell as used herein refers to a host cell into which one or more transgenes have been introduced, typically via transformation of a host cell with a vector.

As used herein, "exogenous" means that the referenced item, such as a molecule, activity or pathway, is added to or introduced into the host cell. For example, an exogenous molecule such as a substrate or cofactor can be added to or introduced into the host cell, e.g., via adding the molecule to the media in or on which a host cell resides. An exogenous nucleic acid sequence can, for example, be introduced either as chromosomal genetic material by integration into a host chromosome or as non-chromosomal genetic material such as a plasmid. Such an exogenous nucleic acid sequence can also be referred to as a "transgene" and may encode an enzyme or enzyme activity which is either heterologous to the host cell in question or which is an endogenous enzyme or enzyme activity in the host cell. Typically, a transgene encoding an endogenous enzyme or enzyme activity provides for overexpression of the enzyme or enzyme activity as compared to the native or parent host cell, i.e., host cell prior to the introduction of the transgene.

In the present context the term "heterologous" means that the referenced item, such as a molecule, activity or pathway, does not normally appear in the host cell, strain or species in question. Typically, a heterologous pathway comprises at least one enzyme or other component which is heterologous to the host cell.

As used herein, the terms "native" or "endogenous" mean that the referenced item is normally present in or native to the host cell or species in question.

As used herein, a "genetic modification" refers to the introduction a genetically inherited change in the host cell genome. Examples of changes include mutations in genes and regulatory sequences, coding and non-coding DNA sequences. "Mutations" include deletions, substitutions and insertions of one or more nucleotides or nucleic acid sequences in the genome. Other genetic modifications include the introduction of heterologous genes or coding DNA sequences by recombinant techniques.

As used herein, "upregulating" an endogenous gene means increasing the transcription and/or translation of a gene present in the native host cell genome relative to a control, such as e.g. the unmodified host cell. Methods of upregulating genes are known in the art and include, e.g., introducing a non-native promoter increasing transcription, modifying the native promoter, deleting genes encoding repressor protein, introducing multiple copies of the gene of interest, etc.

"Downregulating" an endogenous gene as used herein means to reduce, optionally eliminate, the transcription or translation of an endogenous gene so that the levels of functional protein, such as an enzyme, encoded by the gene are significantly reduced in the host cell, typically by at least 50%, such as at least 75%, such as at least 90%, such as at least 95%, as compared to a control. Typically, when the reduced expression is obtained by a genetic modification in the host cell, the control is the unmodified host cell. Sometimes, e.g., in the case of gene deletion, the level of native mRNA and functional protein encoded by the gene is further reduced, effectively eliminated, by more than 95%, such as 99% or greater. Methods of downregulating, disrupting and deleting genes are known to those of skill in the art, and include, e.g., gene disruption or knock-out, site-directed mutagenesis, genomic modifications based on homologous recombination, RNA degradation based on CAS9, etc.

In the present context, "overexpressing" refers to introducing an exogenous nucleic acid sequence, i.e., a transgene, encoding a protein, such as an enzyme, which is either heterologous or native to the host cell, and expressing the transgene to introduce or increase the levels of enzyme activity in the cell as compared to a control, e.g., a native host cell. This can particularly be useful if a host cell does not normally contain the enzymatic activity referred to, where the native enzymatic activity is insufficient, or the native enzyme is subjected to unwanted regulation. Overexpression of a nucleic acid sequence can be achieved by placing the nucleic acid sequence under the control of a promoter, e.g., strong promoter. Non-limiting examples of strong promoters suitable for, e.g., *E. coli* cells are J23101, Ptrc, Plac, PlacUV5, PT7, and PTrp. Non-limiting examples of strong promoters suitable for, e.g., yeast cells are TEF1, PGK1, HXT7 and TDH3. Alternatively, at least for heterologous enzyme activities, a weak promoter can be used to achieve overexpression. Suitable weak promoters are exemplified elsewhere herein.

As used herein, a gene that is a "homolog" or "homologous" to another gene is generally an ortholog (i.e., a descended from the same ancestral sequence but separated when a species diverges into two separate species) or a paralog (i.e., separated by gene duplication within a genome). Typically, homologous genes encode proteins with a moderate to high sequence identity (e.g., at least about 30%, such as at least about 50%, such as at least about 60%, such as at least about 70%, such as at least about 80%, such as at least about 90%, such as at least about 95%, such as at least about 99%, over at least the catalytically active portion, optionally over the full length) and/or can at least partially substitute for the other protein in terms of function, when transferred from one species into another. Homologs of a particular gene can be identified using publicly available and specialized biological databases, e.g., by the eggNOG, InParanoid, OrthoDB, OrthoMCL, OMA, Roundup, TreeFam, LOFT, Ortholuge, EnsemblCompara GeneTrees and HomoloGene.

Unless otherwise stated, the term "sequence identity" for amino acid sequences as used herein refers to the sequence identity calculated as $(n_{ref} - n_{dif}) \cdot 100/n_{ref}$, wherein $n_{dif}$ is the total number of non-identical residues in the two sequences when aligned and wherein $n_{ref}$ is the number of residues in one of the sequences. Hence, the amino acid sequence GSTDYTQNWA will have a sequence identity of 80% with the sequence GSTGYTQAWA ($n_{dif}=2$ and $n_{ref}=10$). The sequence identity can be determined by conventional methods, e.g., Smith and Waterman, (1981), Adv. Appl. Math. 2:482, by the 'search for similarity' method of Pearson & Lipman, (1988), Proc. Natl. Acad. Sci. USA 85:2444, using the CLUSTAL W algorithm of Thompson et al., (1994), Nucleic Acids Res 22:467380, by computerized implementations of these algorithms (GAP, BESTFIT, FASTA, and TFASTA in the Wisconsin Genetics Software Package, Genetics Computer Group). The BLAST algorithm (Altschul et al., (1990), Mol. Biol. 215:403-10) for which software may be obtained through the National Center for Biotechnology Information www.ncbi.nlm.nih.gov/) may also be used. When using any of the aforementioned algorithms, the default parameters for "Window" length, gap penalty, etc., are used.

As used herein, "vector" refers to any genetic element capable of serving as a vehicle of genetic transfer, expression, or replication for an exogenous nucleic acid sequence in a host cell. For example, a vector may be an artificial chromosome or a plasmid, and may be capable of stable integration into a host cell genome, or it may exist as an independent genetic element (e.g., episome, plasmid). A vector may exist as a single nucleic acid sequence or as two or more separate nucleic acid sequences. Vectors may be single copy vectors or multicopy vectors when present in a host cell. Preferred vectors for use in the present invention are expression vector molecules in which one or more functional genes can be inserted into the vector molecule, in proper orientation and proximity to expression control elements resident in the expression vector molecule so as to direct expression of one or more proteins when the vector molecule resides in an appropriate host cell.

Standard recombinant DNA and molecular cloning techniques used here are well known in the art and are described by, e.g., Sambrook, J., Fritsch, E. F. and Maniatis, T. Molecular Cloning: A Laboratory Manual, 4$^{th}$ ed.; Cold Spring Harbor Laboratory: Cold Spring Harbor, N.Y., 2012; and by Silhavy, T. J., Bennan, M. L. and Enquist, L. W. Experiments with Gene Fusions; Cold Spring Harbor Laboratory: Cold Spring Harbor, N.Y., 1984; and by Ausubel, F. M. et al., In Current Protocols in Molecular Biology, published by John Wiley & Sons (1995); and by Datsenko and Wanner (Proc. Natl. Acad. Sci. USA 2000; 97:6640-6645); and by Baba et al. (Mol Syst Biol 2:2006.0008. Epub 2006 Feb. 21); and by Thomason et al. (Curr Protoc Molec Biol 1.16 (2007) and Curr Protoc Molec Biol 1.17 (2007)), and references cited therein. Other useful references are cited elsewhere herein, e.g., in the Examples. Appropriate cells and vectors are available commercially through, for example, the American Type Culture Collection (ATCC), Rockville, Md.

The term "substrate" or "precursor", as used herein in relation to a specific enzyme, refers to a molecule upon which the enzyme acts to form a product. When used in relation to an exogenous biometabolic pathway, the term "substrate" or "precursor" refers to the molecule(s) upon which the first enzyme of the referenced pathway acts. When referring to an enzyme-catalyzed reaction in a cell, an "endogenous" substrate or precursor is a molecule which is native to or biosynthesized by the cell, whereas an "exogenous" substrate or precursor is a molecule which is added to the cell, via a medium or the like.

Enzymes referred to herein can be classified on the basis of the handbook Enzyme Nomenclature from NC-IUBMB, 1992), see also the ENZYME site at the internet: http://www.expasy.ch/enzyme/. This is a repository of information relative to the nomenclature of enzymes, and is primarily based on the recommendations of the Nomenclature Committee of the International Union of Biochemistry and Molecular Biology (IUB-MB). It describes each type of characterized enzyme for which an EC (Enzyme Commission) number has been provided (Bairoch A., The ENZYME database, 2000, Nucleic Acids Res 28:304-305). The IUBMB Enzyme nomenclature is based on the substrate specificity and occasionally on their molecular mechanism.

Specific Embodiments of the Invention

Additional details on the background host cells and SAM-selection methods and other features are provided below.

Background Host Cells

In one aspect, the invention provides a background host cell which is growth-dependent on a metabolite selected from one or more of cysteine and 2-oxobutanoate/isoleucine and comprises a SAM-dependent methyltransferase; a biosynthetic pathway converting SAH to the metabolite via a homocysteine intermediate; and one or more genetic modifications reducing or disrupting any endogenous $H_2S$-dependent and/or L-cysteine-dependent biosynthesis of homocysteine in the cell.

In one aspect, the invention provides a background host cell which is growth-dependent on cysteine and comprises a SAM-dependent methyltransferase; a biosynthetic pathway converting SAH to cysteine via a homocysteine intermediate; and one or more genetic modifications reducing or disrupting any endogenous $H_2S$-dependent and/or L-cysteine-dependent biosynthesis of homocysteine in the cell.

In one aspect, the invention provides a background host cell which is growth-dependent on isoleucine and comprises a SAM-dependent methyltransferase; a biosynthetic pathway converting SAH to isoleucine via a homocysteine intermediate; and one or more genetic modifications reducing or disrupting any endogenous $H_2S$-dependent and/or L-cysteine-dependent biosynthesis of homocysteine in the cell.

In one aspect, the invention provides a background host cell which is growth-dependent on 2-oxobutanoate and comprises a SAM-dependent methyltransferase; a biosynthetic pathway converting SAH to 2-oxobutanoate via a homocysteine intermediate; and one or more genetic modifications one or more genetic modifications reducing or disrupting any endogenous $H_2S$-dependent and/or L-cysteine-dependent biosynthesis of homocysteine in the cell.

In any one of these or other aspects or embodiments described herein, the background host cell may be capable of converting methionine to SAM, e.g., via one or more SAM synthetases (EC 2.5.1.6, FIG. 2). The SAM synthetase may be a native enzyme (such as, e.g., MetK in E. coli and SAM1 and/or SAM2 in yeast) or a SAM synthetase that is heterologous to the host cell.

In any aspect described herein, to make the cell growth-dependent on the metabolite, the cell may be genetically modified to disrupt any endogenous pathway for the biosynthesis of the metabolite other than that from SAH. In some embodiments, the one or more genetic modifications reducing or disrupting any endogenous $H_2S$-dependent and/or L-cysteine-dependent biosynthesis of homocysteine in the cell and the one or more genetic modifications disrupting any endogenous pathway for the biosynthesis of the metabolite are the same, e.g., in the case of a cysE deletion in E. coli.

Typically, although not necessarily, the SAM-dependent methyltransferase is a particular enzyme of interest. The SAM-dependent methyltransferase can be heterologous or endogenous to the host cell, although it is typically expressed from a transgene. In one embodiment, the SAM-dependent methyltransferase is expressed from a heterologous gene. In one embodiment, the SAM-dependent methyltransferase is heterologous to the host cell. In one embodiment, the SAM-dependent methyltransferase is an overexpressed endogenous enzyme. To ensure sufficient expression levels, the expression of the SAM-dependent methyltransferase is preferably under the control of a strong promoter. Non-limiting examples of SAM-dependent methyltransferases that can be used in the SAM-selection systems of the invention include O-methyltransferase (i.e. ASMT), C-methyltransferase, N-methyltransferase and S-methyltransferase. SAM-dependent methyltransferases have been described and characterized, e.g., in Tengg et al. (2012), Lyon and Jacobi (1982) and Attieh et al. (2002).

In particular embodiment, the SAM-dependent methyltransferase is an ASMT. In such embodiments, the host cell may further comprise a 5HTP decarboxylase and a serotonin acetyltransferase, thereby enabling the host cell to convert 5HTP to melatonin.

5HTP decarboxylase is an aromatic L-amino acid decarboxylase (AADC), typically classified as EC 4.1.1.28, which can catalyze the conversion of 5HTP to serotonin. Suitable 5HTP decarboxylases include any tryptophan decarboxylase (TDC) capable of catalyzing the referenced reaction (see, e.g., Park et al., Biosci. Biotechnol. Biocem. 2008; 72(9): 2456-2458.2008, and Gibson et al., J. Exp. Bot. 1972; 23(3):775-786).

Serotonin acetyltransferase, also known as serotonin —N-acetyltransferase, arylalkylamine N-acetyltransferase and AANAT, is typically classified as EC 2.3.1.87. AANAT catalyzes the conversion of acetyl—Examples of suitable sources of ASMT, 5HTP decarboxylase and AANAT are provided in Table 3. The ASMT, 5HTP decarboxylase and AANAT may each be either heterologous or endogenous to the host cell, and may optionally be overexpressed from a transgene, so long as they provide the desired activity in the host cell.

In another particular embodiment, the SAM-dependent methyltransferase is a caffeine synthase, e.g., caffeine synthase 1 (CCS1) from Coffee arabica (UniProtKB: Q8H0D3).

The biosynthetic pathway converting S-adenosylhomocysteine (SAH) to cysteine preferably comprises one or more, preferably all of the following enzyme activities:

(a) a SAH nucleosidase (EC 3.2.2.9), an S-ribosylhomocysteine-lyase (EC 4.4.1.21), a cystathionine-beta-synthase (EC 4.2.1.22) and a cystathionine-gamma-lyase (EC 4.4.1.1); or (b) a SAH hydrolase (EC 3.3.1.1), a cystathionine-beta-synthase (EC 4.2.1.22) and a cystathionine-gamma-lyase (EC 4.4.1.1).

The SAH nucleosidase and S-ribosylhomocysteine-lyase or the SAH hydrolase catalyze the conversion of SAH to homocysteine (FIG. 1 and FIG. 2). Since a SAM cycle is normally present in most cells, the enzymes endogenous to the host cell can be used. If desired, the endogenous genes may be upregulated or overexpressed from a transgene. Alternatively, one or more heterologous genes or transgenes encoding the desired activity can be introduced.

The cystathionine-beta-synthase and cystathionine-gamma-lyase catalyze the conversion of homocysteine to cysteine (FIG. 1). For host cells where these enzymes are endogenous, e.g., S. cerevisiae, C. glutamicum, S. coelicolor and S. griseus (see Table 2), the endogenous enzyme can be used, although the endogenous genes may optionally be upregulated or overexpressed. In cases where the initial host cell lacks one or both enzymes, such as, e.g., E. coli, R. eutropha and C. acetylbutylicum, heterologous enzymes can be introduced via transformation with transgenes to introduce the desired activity. In one embodiment, the transgenes encode one or both of S. cerevisiae cystathionine-beta-synthase (CYS3) and cystathionine-gamma-lyase (CYS4), which were also used in the Examples to introduce the activity into E. coli host cells. Examples of suitable sources of cystathionine-beta-synthase and cystathionine-gamma-lyase are provided in Table 3.

The background host cell further comprises one or more genetic modifications reducing or disrupting endogenous $H_2S$-dependent and/or L-cysteine-dependent biosynthetic pathways in the initial host cell. Thus, the biosynthetic pathway described above becomes the dominant or only significant source of homocysteine in the background host cell. Preferably, the genetic modifications comprise the downregulation or deletion of at least one endogenous gene encoding an enzyme of the $H_2S$-dependent and/or L-cysteine-dependent pathway. Non-limiting examples of genes or enzyme activities to downregulate or delete, e.g., knock-out; in exemplary host cells are provided in Table 1 and FIG. 3. Other gene or genes to downregulate or delete, as well as homologs or orthologs of the gene in other species than those listed here, can be identified and, if needed, tested, by the skilled person according to known methods. For example, to determine whether a particular genetic modification reduces or disrupts endogenous homocysteine biosynthesis, a cysteine auxotrophic strain can be prepared. Cystathionine-beta and gamma enzymes-dependent growth would then be observed only upon external homocysteine feeding.

Preferably, the one or more genetic modifications reduce the amount or production rate of endogenous $H_2S$- and/or L-cysteine-dependent biosynthesis of homocysteine by at least 80%, such as at least 90%, such as about 95% or more, as compared to a control. The one or more genetic modifications may additionally disrupt endogenous $H_2S$- and/or L-cysteine-dependent biosynthesis, reducing the amount or production rate of endogenously biosynthesized homocysteine by more than 95%, such as about 98%, about 99% or more, such as about 100%, as compared to a control.

Whether one or more genetic modifications reduce and/or disrupt endogenous $H_2S$- and/or L-cysteine-dependent biosynthesis of homocysteine can be assessed by directly measuring the level of homocysteine in the genetically modified cell as compared to the control, e.g., the parent or native cell without the one or more genetic modifications, using standard analytical techniques as described by Bennett et al. (2009). Alternatively, the effect of one or more genetic modifications on homocysteine production can be evaluated indirectly by measuring the reduction in the growth rate of the genetically modified cell as compared to a control. Typically, in the absence of exogenously added homocysteine and metabolites (i.e., in the absence of exogenously added cysteine, 2-oxobutanoate and isoleucine) one or more genetic modifications resulting in a reduction in growth rate by at least 80%, such as at least 90%, such as about 95% or more, as compared to a control. In cases where the one or more genetic modifications disrupts endogenous $H_2S$- and/or L-cysteine-dependent homocysteine biosynthesis, the growth rate may be reduced by more than 95%, such as about 98%, about 99% or more, such as nearly 100%, as compared to the control. The control may be, for example, the growth rate of the unmodified parent or native cell or the growth rate of the genetically modified cell in the presence of an externally added surplus of metabolites, i.e., homocysteine; homocysteine and cysteine; homocysteine, cysteine and 2-oxobutanoate; or homocysteine, cysteine, and isoleucine.

In one embodiment, the background host cell is, or is derived from, a bacterial cell and is growth-dependent on cysteine, the one or more genetic modifications comprising a downregulation or deletion of one or more endogenous genes encoding one or more of a serine acetyltransferase (EC 2.3.1.30), a cystathionine-beta-lyase (EC 4.4.1.8), acetylhomoserine sulfhydrylase (EC 2.5.1.49), a homoserine acetyltransferase (EC 2.3.1.31), a homoserine succinyltransferase (EC 2.3.1.46), a succinylhomoserine(thiol) lyase (EC 2.5.1.48) or a cysteine synthase (EC 2.5.1.47), or a combination thereof. In one embodiment, the one or more genetic modifications comprise a downregulation or deletion of an endogenous gene encoding a serine acetyltransferase (EC 2.3.1.30), such as cysE or metX; a cysteine synthase such as one or both of cysK and cysM; a homoserine succinyltransferase such as metA; a succinylhomoserine(thiol)lyase such as metB; or a cystathionine-beta-lyase such as one or both of metC and malY. In a particular embodiment, the background host cell is, or is derived from, an E. coli, B. subtilis, C. glutamicum, R. eurotropha or C. acetobytylicum cell wherein the one or more endogenous genes are downregulated or deleted, e.g., knocked-out. In a specific embodiment, the background host cell is an E. coli cell, growth-dependent on cysteine and comprising a downregulation or deletion, e.g., a knock-out, of cysE.

In one embodiment, the background host cell is also or alternatively growth-dependent on 2-oxobutanoate and/or isoleucine, and the one or more genetic modifications further comprise a downregulation or deletion of an endogenous gene encoding a threonine ammonia-lyase (4.3.1.19). In a particular embodiment, the background host cell is an E. coli cell growth-dependent on cysteine, 2-oxobutanoate and isoleucine, comprising a downregulation or deletion, e.g., a knock-out, of cysE and one or both of ilvA and tdcB. In another embodiment, the background host cell is an E. coli cell growth-dependent on cysteine, 2-oxobutanoate and isoleucine, comprising a downregulation or deletion, e.g., a knock-out, of cysE, ilvA and tdcB. In another embodiment, the background host cell is an E. coli cell growth-dependent on cysteine, 2-oxobutanoate and isoleucine, comprising a downregulation or deletion, e.g., a knock-out, of cysE, ilvA, tdcB and MetA. In another embodiment, the background host cell is an *E. coli* cell growth-dependent on cysteine, 2-oxobutanoate and isoleucine, comprising a downregulation or deletion, e.g., a knock-out, of cysE, ilvA, tdcB and MetB. In another embodiment, the background host cell is an *E. coli* cell growth-dependent on cysteine, 2-oxobutanoate and isoleucine, comprising a downregulation or deletion, e.g., a knock-out, of cysE, ilvA, tdcB, MetA and MetB.

In one embodiment, the background host cell is a yeast cell and is growth-dependent on cysteine, the one or more genetic modifications comprising a downregulation or deletion of an endogenous gene encoding an acetylhomoserine sulfhydrylase (EC 2.5.1.49), optionally MET17, or a homoserine O-acetyltransferase (EC 2.3.1.31), optionally MET2, or a combination thereof. In a particular embodiment, the background host cell is an *S. cerevisiae* cell.

In one embodiment, the background host cell is a yeast cell also or alternatively growth-dependent on 2-oxobutanoate and/or isoleucine, and the one or more genetic modifications comprise a downregulation or deletion of one or both of an acetylhomoserine sulfhydrylase (EC 2.5.1.49), optionally MET17, or a homoserine O-acetyltransferase (EC 2.3.1.31), optionally MET2, and one or both of a L-serine/L-threonine dehydratase, optionally CHA1, and a threonine dehydratase, optionally ILV1. In a particular embodiment, the yeast cell is a *S. cerevisiae* cell.

In one embodiment, the background host cell is a plant cell, and is growth-dependent on cysteine, the one or more genetic modifications comprising a downregulation or deletion of an endogenous gene encoding a cysteine synthase (EC 2.5.1.47), optionally one or more of oasA1, oasB, AT3G61440.1, such as both of oasA1 and oasB. In a particular embodiment, the background host cell is derived from an *A. thaliana* cell. In one embodiment, the background cell is also or alternatively growth-dependent on 2-oxobutanoate and/or isoleucine, and the one or more genetic modifications comprise a downregulation or deletion of a threonine ammonia-lyase (EC 4.3.1.19), optionally AT3G10050.1. In a particular embodiment, the background host cell is derived from an *A. thaliana* cell.

In further aspects, the background host cell may also comprise genetic modifications downregulating or deleting one or more endogenous SAM-dependent methyltransferases or other enzymes competing with the SAM-dependent methyltransferase present in the initial host cell. In one embodiment, the background host cell has further been modified so as to downregulate or delete a native gene encoding a cyclopropane fatty acyl phospholipid synthase. As indicated in Example 1, without being limited to theory, downregulating or deleting a gene corresponding to the cfa gene in a bacterial host cell improves SAM availability to the SAM-dependent methyltransferase of interest. The amino acid sequence of the Cfa protein and the location of the cfa gene in the *E. coli* genome are known in the art (see NCBI Reference Sequence: NP_416178.1 and references cited therein). Orthologs to the cfa gene in *E. coli* exist in, e.g., *C. glutamicum* ATCC 13032 (cma). Accordingly, cfa (*E. coli*) or cma (*C. glutamicum*) or homologs or orthologs thereof may be downregulated in bacterial host cells. Likewise, MET6 in *S. cerevisiae* or homocysteine methyltransferase homologs or orthologs in other yeast host cells may be downregulated or deleted. In another embodiment, one or more of ERG6, CHO2, OPI3, SET2, SET1 and DOT1 are also or alternatively deleted.

So, in separate and specific embodiments, a genetically modified bacterial cell comprises a SAM-dependent methyltransferase, a heterologous cystathionine-beta-synthase, a heterologous cystathionine-gamma-lyase, and (a) a downregulation or deletion of cysE;
(b) a downregulation or deletion of cysK and cysM;
(c) a downregulation or deletion of cysE and ilvA;
(d) a downregulation or deletion of cysE and tdcB;
(e) a downregulation or deletion of cysE, ilvA and tdcB;
(f) a downregulation or deletion of cysE, ilvA, tdcB, and metA;
(g) a downregulation or deletion of cysE, ilvA, tdcB, and metB;
(h) a downregulation or deletion of metA, ilvA and tdcB;
(i) a downregulation or deletion of metB, ilvA and tdcB;
(j) a downregulation or deletion of metC, malY, ilvA and tdcB;
(k) a downregulation or deletion of metC, malY, ilvA, tdcB and metA;
(l) a downregulation or deletion of metC, malY, ilvA, tdcB and metB; or
(m) any one of (a) to (l), further comprising a downregulation or deletion of cfa.

The background host cell may, for example, be a genetically modified cell derived from an *Escherichia* cell and comprising a SAM-dependent methyltransferase, a heterologous cystathionine-beta-synthase, a heterologous cystathionine-gamma-lyase, and a downregulation or deletion of cysE and, optionally, cfa.

In another embodiment, the background host cell is a genetically modified cell derived from a *Saccharomyces* cell and comprising a SAM-dependent methyltransferase which is heterologous or overexpressed as compared to the native *Saccharomyces* cell and (a) a downregulation or deletion of MET17;
(b) a downregulation or deletion of MET2;
(c) a downregulation or deletion of MET2 and MET17
(d) a downregulation or deletion of MET17, CHA1 and ILV1;
(e) a downregulation or deletion of MET2, CHA1 and ILV1;
(f) a downregulation or deletion of MET17, MET2, CHA1 and ILV1; or
(g) any one of (a) to (f), further comprising a downregulation or deletion of MET6, or
(h) any one of (a) to (g), further comprising a downregulation or deletion of one or more native SAM-dependent methyltransferases, optionally selected from one or more of ERG6, CHO2, OPI3, SET2, SET1 and DOT1.

For example, the native SAM-dependent methyltransferase(s) to downregulate or delete may comprise an enzyme selected from ERG6, CHO2, OPI3, SET2, SET1 and DOT1, or a combination of enzymes selected from CHO2, OPI3 and SET2; CHO2, OPI3, SET1 and SET2; OPI3, SET1 and SET2; CHO2, OPI3, SET2, SET1 and DOT1; ERG6, CHO2, OPI3 and SET2; ERG6, CHO2, OPI3, SET1 and SET2; ERG6, OPI3, SET1 and SET2; and ERG6, CHO2, OPI3, SET2, SET1 and DOT1. In one particular embodiment, the native SAM-dependent methyltransferase(s) to downregulate or delete is CHO2, OPI3 or a combination of both. In one particular embodiment, the native SAM-dependent methyltransferase(s) to downregulate or delete is or comprises a histone methyltransferase.

Depending on which native SAM-dependent methyltransferase(s) is/are downregulated or deleted, it may be advantageous to provide the cell with one or more exogenous compounds to replace one or more metabolites synthesized by a pathway in which the downregulated or deleted SAM-dependent methyltransferase normally takes part. The compound(s) in question that is/are necessary for the growth of well-characterized cells such as *E. coli*, *S. cerevisiae*, etc. are typically known to a person of skill in the art, or can be determined experimentally. For example, for a yeast host cell in which CHO2 and/or OPI3 is downregulated or deleted, choline can be added to the growth or selection medium, e.g., at a concentration of about 0.1 mM, about 1 mM or about 10 mM. Similarly, for a yeast host cell in which ERG6 is downregulated or deleted, ergosterol can be added to the growth or selection medium, e.g., at a concentration of about 0.001 mM, about 0.01 mM, about 0.1 mM, about 1 mM or about 10 mM.

Provided are also vectors for the genetic transfer, expression, or replication of one, two or more transgenes to be expressed in a background host cell according to the invention.

The specific design of the vector(s) depends on, e.g., whether initial host cell already endogenously produces sufficient amounts of one or more of the enzymes expressed by the transgenes. For example, in an *S. cerevisiae* host cell, it may not be necessary to introduce a transgene encoding a cystathionine-gamma-lyase and/or a cystathionine-beta-synthase, in case sufficient amounts of the enzyme is expressed from the native gene or in case the endogenous gene is upregulated. Additionally, for transformation of a particular host cell, two or more vectors with different combinations of the enzymes used in the present invention can be applied. Accordingly, the nucleic acid sequences encoding the SAM-dependent methyltransferase and one or more of a SAH nucleosidase, an 5-ribosylhomocysteine-lyase, a SAH hydrolase, a cystathionine-beta-synthase and a cystathionine-gamma-lyase may be located on the same vector, or on two or more different vectors. The vector can be a plasmid, phage vector, viral vector, episome, an artificial chromosome or other polynucleotide construct, and may, for example, include one or more selectable marker genes and appropriate expression control sequences.

Generally, regulatory control sequences are operably linked to the encoding nucleic acid sequences, and include constitutive, regulatory and inducible promoters, transcription enhancers, transcription terminators, and the like which are well known in the art. The encoding nucleic acid sequences can be operationally linked to one common expression control sequence or linked to different expression control sequences, such as one inducible promoter and one constitutive promoter.

The promoter sequence is typically one that is recognized by the intended host cell. For an *E. coli* host cell, suitable promoters include, but are not limited to, the lac promoter, the T7 promoter, pBAD, the tet promoter, the Lac promoter, the Trc promoter, the Trp promoter, the recA promoter, the λ (lamda) promoter, and the PL promoter. Preferred promoters include the Trc promoter. For *Streptomyces* host cells, suitable promoters include that of *Streptomyces coelicolor* agarase (dagA). For a *Bacillus* host cell, suitable promoters include the sacB, amyL, amyM, amyQ, penP, xylA and xylB. Other promoters for bacterial cells include prokaryotic beta-lactamase (Villa-Kamaroff et al., 1978, Proceedings of the National Academy of Sciences USA 75: 3727-3731), and the tac promoter (DeBoer et al., 1983, Proceedings of the National Academy of Sciences USA 80: 21-25). For an *S. cerevisiae* host cell, useful promoters include, but are not limited to, the TEF1, HXT7, TDH3, RNR2, ENO-1, GAL1, RPL18B, PGI1, TRX2, REV1, RNR2, CYC1, ADH1, ADH2, GAP, TPI, CUP1, PHO5 and PGK, such as PGK1 promoters. Other useful promoters for yeast host cells are described by Romanos et al., 1992, Yeast 8: 423-488. Still other useful promoters for various host cells are described in "Useful proteins from recombinant bacteria" in Scientific American, 1980, 242: 74-94; and in Sambrook et al., 2012, supra.

In one specific embodiment, the host cell is an *E. coli* host cell and one or more or all of the transgenes is under the control of a strong promoter, e.g., each separately selected from J23101, Trc, lac, lacUV5, Trp, T7, trac and PL promoter. In one specific embodiment, the host cell is an *S. cerevisiae* host cell and one or more or all of the transgenes is under the control of a strong promoter, e.g., each separately selected from PGK1, TEF1, HXT7 and TDH3. In one specific embodiment, the host cell is an *S. cerevisiae* host cell and one or more or all of the transgenes is under the control of a weak promoter, e.g., RNR2 or REV1.

The background host cell can be prepared according to the aspects and embodiments described herein. Typically, the host cell is prepared by genetically modifying the native or "initial" host cell cells as described and, optionally, introducing transgenes as described, e.g., via transformation with one or more vectors according to any preceding embodiment, using standard methods known in the art and cited elsewhere herein.

The genetic modifications to the host cell genome to reduce any endogenous $H_2S$-dependent and/or L-cysteine-dependent biosynthesis of homocysteine and/or reduce any endogenous can be made before, simultaneously or after the introduction of the vector(s). As used herein, a "genetic modification" refers to the introduction a genetically inherited change in the host cell genome, such as mutations in genes and regulatory sequences. Genetic modifications resulting in a reduced expression of a target gene/protein can include, e.g., a downregulation of the gene (e.g., a mutation in a promoter that results in reduced or disrupted gene expression), a deletion of the gene (e.g., a mutation or deletion of the gene that results in 95% or greater decrease in gene expression), a mutation or deletion in the coding sequence which results in the expression of non-functional protein, and/or the introduction of a nucleic acid sequence that reduces the expression of the target gene, e.g. a repressor that inhibits expression of the target or inhibitory nucleic acids (e.g. CRISPR etc.) that reduces the expression of the target gene.

The vector(s), once introduced, may be maintained as a chromosomal integrant or as a self-replicating extra-chromosomal vector. Preferably, for transformation of an *E. coli* or other bacterial host cell, the vectors are designed as follows: A promoter is used to control the expressions of a gene or an artificial operon containing up to three genes connected with a linker sequence, in order to express the genes at a suitable level so that the introduction of heterologous genes/pathways do not overdraw substrates or energy in the host cell. In one particular embodiment, the host cell, preferably derived from a bacterial cell, is transformed according to a strategy outlined in the Examples.

In one embodiment, for transformation of a yeast host cell such as *S. cerevisiae*, the heterologous genes are provided on a plasmid. In another embodiment, the heterologous genes are integrated onto the chromosome using homologous recombination. As compared with gene expression based on plasmids, the chromosomal integrated genes may be expressed with higher fidelity and resulted in better protein translation, in particular for multiple gene co-expression systems.

The transformation can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product, including those referred to above, e.g., relating to measurement of 5HTP production. Expression levels can further be optimized to obtain sufficient expression using methods well known in the art and as disclosed herein.

The background host cell may be prepared from any type of initial host cell, e.g., from a microbial, insect or plant host cell.

The initial host cell need not necessarily be a wild-type cell, i.e., it may already have some modification to the genome, e.g., expressing one or more transgenes or having some mutation in an endogenous gene. For example, the initial host cell may be a producer cell or cell line for a compound of interest and the SAM-selection system introduced to improve the SAM-dependent methyltransferase activity in the cell.

In one embodiment, the initial host cell is a microbial cell. The microbial host cell for use in the present invention is typically unicellular and can be, for example, a bacterial cell, a yeast host cell, a filamentous fungal cell, or an algal cell. Examples of suitable host cell genera include, but are not limited to, *Acinetobacter, Agrobacterium, Alcaligenes, Anabaena, Aspergillus, Bacillus, Bifidobacterium, Brevibacterium, Candida, Chlorobium, Chromatium, Corynebacteria, Cytophaga, Deinococcus, Enterococcus, Erwinia, Erythrobacter, Escherichia, Flavobacterium, Hansenula, Klebsiella, Lactobacillus, Methanobacterium, Methylobacter, Methylococcus, Methylocystis, Methylomicrobium, Methylomonas, Methylosinus, Mycobacterium, Myxococcus, Pantoea, Phaffia, Pichia, Pseudomonas, Rhodobacter, Rhodococcus, Saccharomyces, Salmonella, Sphingomonas, Streptococcus, Streptomyces, Synechococcus, Synechocystis, Thiobacillus, Trichoderma, Yarrowia* and *Zymomonas*.

In one embodiment, the initial host cell is bacterial cell, e.g., an *Escherichia* cell such as an *Escherichia coli* cell; a *Bacillus* cell such as a *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, or a *Bacillus thuringiensis* cell; or a *Streptomyces* cell such as a *Streptomyces lividans* or *Streptomyces murinus* cell. In a particular embodiment, the background host cell is derived from cell of the *Escherichia* genus, such as an *Escherichia coli* cell. In another particular embodiment, the host cell is of an *E. coli* strain selected from the group consisting of K12.DH1 (Proc. Natl. Acad. Sci. USA, volume 60, 160 (1968)), JM101, JM103 (Nucleic Acids Research (1981), 9, 309), JA221 (J. Mol. Biol. (1978), 120, 517), HB101 (J. Mol. Biol. (1969), 41, 459) and C600 (Genetics, (1954), 39, 440).

In one embodiment, the initial host cell is a fungal cell, such as, e.g., a yeast cell. Exemplary yeast cells include *Candida, Hansenula, Kluyveromyces, Pichia, Saccharomyces, Schizosaccharomyces* and *Yarrowia* cells. In a particular embodiment, the host cell is an *S. cerevisiae* cell. In another particular embodiment, the host cell is of an *S. cerevisie* strain selected from, but not limited to, the group consisting of *S. cerevisiae* KA31, AH22, AH22R-, NA87-11A, DKD-5D, 20B-12, AL1, AL3-h, CA1, CBS7960, CEN.PK113-7D, CLIB215, CLIB324, CLIB382, DBVPG1373, DBVPG1788, DBVPG6044, DBVPG6765, Ethanol Red, GDB 135-h, GDB 325, GDB 379, KK:YS2-h, L.1528, LUI250, NCYC110, PWS, RM11, S288c, SK1, T7, T73, UWOPS03-461.4, UWOPS05-217.3, UWOPS05-227.2, Y10, Y55, YJM269, YJM975, YJM978, YPS128 and YPS606, or a derivative of any thereof. Suitable examples of other yeast host cell strains include *S. pombe* NCYC1913 and NCYC2036 and *Pichia pastoris* KM71.

In one embodiment, the initial host cell is an *Escherichia, Saccharomyces*, a *Corynebacterium*, a *Bacillus*, a *Clostridium*, a *Ralstonia*, or a *Streptomyces* cell. In separate and specific embodiments, the host cell is an *E. coli, S. cerevisiae, B. subtilis, C. glutamicum, S. coelicolor, S. griseus, R. eutropha* or *C. acetobutylicum* cell.

In one embodiment, the initial host cell is a plant cell, such as, e.g., an *Arabidopsis thaliana* or *Medicago sativa* cell.

Also provided are compositions or a strain comprising a plurality of a background host cell according to any aspect or embodiment described herein.

Applications for the SAM-Selection System

The invention also relates to methods of using the background host cells according to the aspects and embodiments described herein to evolve the SAM-dependent methyltransferase activity of a background host cell under selection pressure (i.e., no supplementation with cysteine, 2-oxobutanoate and/or isoleucine, as applicable). These methods may further comprise selecting and/or producing evolved cells, identifying the genomic and/or proteomic changes that have occurred in the evolved cell so that these can be transferred to and tested in other host cells, and using the evolved cells in the production of methylated compounds.

The evolution of a background host cell preferably takes place in a minimal medium supplemented with an abundance of methionine, a simple carbon source (e.g., glucose) and a substrate or substrate precursor of the SAM-dependent methyltransferase at culture conditions suitable for growth. Suitable temperatures are, for example, in the range of 30-37° C.

Methionine may be added at, e.g., a concentration of at least about 0.05 g/l, such as at least about 0.1 g/l, such as at least about 0.15 g/l, at least about 0.2 g/l, at least about 0.5 g/l, or at least about 1 g/l. For example, the concentration of methionine may be in the range of about 0.05 g/l to about 1 g/l, such as in the range of about 0.1 g/l to about 0.5 g/l. Substrate or substrate precursor may be added at, e.g., a molar ratio with methionine ranging from about 1:2 to about 2:1, such as from about 1:1.5 to about 1.5:1, such as approximately 1:1 or equimolar concentrations. For example, if the SAM-dependent methyltransferase is an ASMT and the concentration of methionine is about 0.15 g/L, the substrate precursor 5HTP can be included at a concentration of about 1 mM. Glucose may be included at a concentration of at least about 0.1% (w/v), such as at least about 0.2% (w/v), such as at least about 0.5% (w/v), such as at least about 1% (w/v), such as at least about 1.5% (w/v), such as at least about 2% (w/v) such as at least about 4% (w/v). For example, the concentration of glucose may be in the range of about 0.1% to about 4% (w/v), such as in the range of about 0.2% to about 2% (w/v). Specific, non-limiting examples of suitable minimal media for bacterial cells include M9 minimum media containing minimal salts, optionally vitamins, and 0.2% glucose (w/v). Specific, non-limiting examples of suitable minimal media for a yeast cell such as *S. cerevisiae* include yeast nitrogen base and Delft minimal media containing minimal trace metals, vitamins, and 2% glucose (w/v). The minimal medium is normally not supplemented with cysteine, 2-oxobutanoate and/or isoleucine during the evolution. However, as described elsewhere herein, compounds such as choline, ergosterol, etc. may also be added to the medium in order to replace metabolites no longer synthesized by the host cell because of a downregulation or deletion of a gene encoding a native SAM-dependent methyltransferase, i.e., a SAM-sink.

In some embodiments, prior to the evolution or other testing step, it may be advantageous to subject background host cells to 'starvation' to ensure that any internal methionine, cysteine, isoleucine and/or 2-oxobutanoate etc. is depleted before the evolution or other testing. In such cases the host cell may, for example, be incubated in minimal medium for a period of about 0.5 h, about 1 h, about 6 h, about 12 h, about 24 h or more, e.g., about 27 h. In one embodiment, the host cells prepared for the starvation step are in growth phase, e.g., harvested in or near mid-log phase.

The evolution can be permitted to occur for any suitable period of time, e.g., 1 week, 2 weeks, 4 weeks, 8 weeks or more. An evolved cell or clone can then be identified as one having an increased growth rate.

Also provided are compositions comprising a genetically modified cell as described in any aspect or embodiment herein. In one embodiment there is provided a composition comprising a plurality of a genetically modified cell. In one embodiment, the composition comprises a culture medium comprising methionine, at least one substrate or substrate precursor of the SAM-dependent methyltransferase, and a carbon source. In one embodiment, the composition comprises methionine at a concentration of at least about 0.05 g/l, such as at least about 0.1 g/l, such as at least about 0.15 g/l, at least about 0.2 g/l, at least about 0.5 g/l, or at least about 1 g/l. For example, the concentration of methionine may be in the range of about 0.05 g/l to about 1 g/l, such as in the range of about 0.1 g/l to about 0.5 g/l. The concentration of substrate or substrate precursor may be at a molar ratio with methionine ranging from about 1:2 to about 2:1, such as from about 1:1.5 to about 1.5:1, such as approximately 1:1 or equimolar concentrations. For example, if the SAM-dependent methyltransferase is an ASMT and the concentration of methionine is about 0.15 g/L, the concentration of the substrate precursor SHIP can be about 1 mM. In one embodiment, the carbon source is glucose at a concentration of at least about 0.1% (w/v), such as at least about 0.2% (w/v), such as at least about 0.5% (w/v), such as at least about 1% (w/v), such as at least about 1.5% (w/v), such as at least about 2% (w/v) such as at least about 4% (w/v). For example, the concentration of glucose may be in the range of about 0.1% to about 4% (w/v), such as in the range of about 0.2% to about 2% (w/v). In one embodiment, the composition is substantially free of homocysteine, cysteine, 2-oxobutanoate and/or isoleucine.

Specifically, since the SAM-system is designed as a growth-selection method, an "evolved" or "improved" SAM-dependent methyltransferase activity of a cell means can be identified as having a growth (i.e., multiplication) which is increased as compared to a control, e.g., the background host cell prior to the evolution, which is usually barely able to grow in the absence of added cysteine, 2-oxobutanoate and/or isoleucine.

An increased growth rate can be, for example, at least 5%, such as at least 10%, such as at least 20%, such as at least 50%, such as at least 75% such as at least 100%, such as at least 200%, such as at least 300%, such as at least 400%, such as at least 500% higher than that of the control.

In one embodiment, an evolved cell is identified as having a growth rate of at least about 0.05 $h^{-1}$, such as at least about 0.1 $h^{-1}$, such as at least about 0.2 $h^{-1}$, such as at least about 0.3 $h^{-1}$, such as at least about 0.5 $h^{-1}$, such as about 0.7 $h^{-1}$ or higher, such as about 1.0 $h^{-1}$ or higher, such as between about 0.05 $h^{-1}$ and about 1.0 $h^{-1}$, such as between about 0.05 $h^{-1}$ and about 0.7 $h^{-1}$ under the evolution conditions described above, e.g., in minimal medium (e.g., M9 or Delft) supplemented with about 0.15 g/L of methionine, a simple carbon source (e.g., glucose at about 2 g/L) and a substrate or substrate precursor of the SAM-dependent methyltransferase at about equimolar concentrations with methionine, in batch culture at a temperature suitable for growth, e.g., about 30° C. Preferably, the growth rate of evolved or improved cells is comparable to or higher than the growth rate of the prototrophic version of the background host strain or the wild-type growth rate (for example, about 0.7 $h^{-1}$ for wild-type E. coli and about 0.4 $h^{-1}$ for wild-type S. cerevisiae).

Alternatively, since the background host cell is usually barely able to grow in the absence of added cysteine, 2-oxobutanoate and/or isoleucine, an evolved or improved SAM-dependent methyltransferase activity can be identified by simply observing which cell cultures are capable of growing in the absence of added cysteine, 2-oxobutanoate and/or isoleucine after a suitable period of time (see Examples).

As already described, once an evolved cell has been identified, the genomic and/or proteomic changes or mutations that occurred in the evolved cell can be identified by well-known analytical methods, and then transferred into another cell of choice, typically of the same or a similar genus, species or strain. This may, for example, be a producer cell where improved SAM-dependent methylation activity is desired.

Alternatively, the evolved cell may itself be directly applied for fermentation, where the improved SAM-dependent methylation can be exploited for production purposes. The use of the evolved cell for fermentation may indeed be advantageous. This because the operation of the SAM-cycle is resource-demanding, requiring one molecule of ATP and methionine per turnover (see FIG. 2). In an evolved cell, however, the cooperation between the intended heterologous pathway and the native metabolic networks has been fine-tuned. It is therefore typically only possible to reach the maximum turnover of the SAM-cycle under selective conditions; if the selection pressure was relieved, a sub-optimal turnover of the SAM-cycle could occur and hence reduce methylated product formation. Furthermore, production of methylated products is directly coupled to biomass production under selective conditions.

Thus, fermentation optimization parameters can be simplified towards biomass formation rather than towards a specific production.

Fermentation using evolved cells under selective conditions preferably takes place in a fermentation medium supplemented with a sufficient amount of methionine, a simple carbon source (e.g., glucose, lactic acid and/or galactose) and a substrate or substrate precursor of the SAM-dependent methyltransferase, at suitable growth conditions (e.g., a temperature, pH and oxygen suitable for growth), e.g., at similar conditions as described for evolution in any one of the preceding embodiments.

TABLE 3

Sequence information

| Name (EC #) | Species | NCBI or UniProtKB accession No. (SEQ ID) |
|---|---|---|
| Cystathionine-gamma-lyase (EC 4.4.1.1) | S. cerevisiae (CYS3) | NP_009390.1NP (1) |
| | C- glutamicum | WP_011014447.1 (2) |
| | S. coelicolor | WP_011029309.1 (3) |
| | S. griseus | BAG20489.1 (4) |
| | B. subtilis | WP_003229810.1 (5) |
| | H. sapiens | P32929-1 (6) |
| Cystathionine-beta-synthase (EC 4.2.1.22) | S. cerevisiae (CYS4) | NP_011671.3NP (7) |
| | S. coelicolor | WP_011028755.1 (8) |
| | S. griseus | WP_003968679.1 (9) |
| | C. acetobutylicum | WP_034580948.1 (10) |
| | Arabidopsis thaliana | Q6NKY5 (11) |
| | Homo sapiens | P35520-1 (12) |
| L-tryptophan hydroxylase (EC 1.14.16.4) (TPH) | Oryctolagus cuniculus TPH1 | P17290-1, v2 |
| | Homo sapiens TPH1 | NP_004170.1 |
| | Homo sapiens TPH2 | NP_775489.2 |
| | Gallus gallus | NP_990287.1 |
| | Mus musculus | NP_033440.1 |
| | Equus caballus | NP_001075252.1 |
| | Schistosoma mansoni | AAD01923.1 |
| acetylserotonin O-methyltransferase (EC 2.1.1.4) (ASMT) | Homo sapiens | P46597-1, v1 |
| | Ocimum basilicum | Q9XGV9-1, v1 |
| | Bos taurus | P10950-1, v2 |
| | Takifugu rubripes | XP_011609423.1 |
| | Macaca mulatta | NP_001028112.1 |
| | Elephantulus edwardii | XP_006902482.1 |
| | Oryza sativa | XP_015610997.1 |
| | Rattus norvegicus | NP_653360.2 |
| | Gallus gallus | NP_990674.1 |
| | Chromobacterium violaceum | WP_011135808.1 |
| | Desulfotomaculum kuznetsovii DSM 6115 | YP_004515712.1 |
| | Xenopus (Silurana) tropicalis | NP_001011409.1 |
| | Pseudomonas fluorescens | WP_019095725.1 |
| | Candidatus Solibacter usitatus | WP_011682595.1 |
| | Fenneropenaeus chinensis | AAZ66373.1 |
| | Arabidopsis thaliana | NP_200227.1 |
| 5HTP decarboxylase (EC 4.1.1.28) | Acidobacterium capsulatum | WP_015898075.1 |
| | Rattus norvegicus | XP_006251536.1 |
| | Sus scrofa | NP_999019.1 |
| | Homo sapiens | P20711-1, v2 |
| | Capsicum annuum | NP_001312016.1 |
| | Drosophila caribiana | AAM80956.1 |
| | Maricaulis maris (strain MCS10) | ABI65701.1 |
| | Oryza sativa subsp. Japonica | XP_015648768.1 |
| | Pseudomonas putida S16 | WP_013972057.1 |
| | Catharanthus roseus | P17770-1, v1 |
| serotonin acetyltransferase (EC 2.3.1.87 or 2.3.1.5) (AANAT) | Chlamydomonas reinhardtii | BAH10512.1 |
| | Bos Taurus, optionally with A55P mutation | DAA18183.1 |
| | Gallus gallus | NP_990489.1 |
| | Homo sapiens | NP_001079.1 |
| | Mus musculus | XP_011246971.1 |
| | Oryctolagus cuniculus | XP_008249128.1 |
| | Ovis aries | NP_001009461.1 |
| caffeine synthase | Coffea arabica | Q8H0D3 |
| cysE | E. coli | P0A9D4 |
| ilvA | E. coli | P04968 |
| tdcB | E. coli | P0AGF6 |
| metA | E. coli | P07623 |
| metB | E. coli | P00935 |
| cfa | E. coli | P0A9H7 |
| cysK | E. coli | P0ABK5 |
| cysM | E. coli | P16703 |
| metC | E. coli | P06721 |
| malY | E. coli | P23256 |
| MET2 | S. cerevisiae | P08465 |
| MET17 | S. cerevisiae | P06106 |
| CHA1 | S. cerevisiae | P25379 |
| ILV1 | S. cerevisiae | P00927 |
| MET6 | S. cerevisiae | P05694 |
| ERG6 | S. cerevisiae | P25087 |
| CHO2 | S. cerevisiae | P05374 |
| OPI3 | S. cerevisiae | P05375 |
| SET2 | S. cerevisiae | P46995 |
| SET1 | S. cerevisiae | P38827 |
| DOT1 | S. cerevisiae | Q04089 |

Example 1

Strains

The background strain HMP112 is derived from BW25113. When required, genomic modification was achieved by means of lambda red recombination or P1 transduction using KEIO collection strains as a genetic element donor.

Media and Growth Conditions

All strains were maintained at 37° C. in LB (Lennox) Broth (Sigma-Aldrich), 2×YT or M9 minimum media containing 1×M9 minimal salts (BD Difco™), 2 mM $MgSO_4$, 100 μM $CaCl_2$, 500-fold diluted trace minerals (10 g/l $FeCl_3.6H_2O$, 2 g/l $ZnSO_4.7H_2O$, 0.4 g/l $CuCl_2.2H_2O$, 1 g/l $MnSO_4.H_2O$, 0.6 g/l $CoCl_2.6H_2O$, and 1.6 mM EDTA, pH 8.0), 1×ATCC® Vitamin Supplement (ATCC MD-VS™), and 0.2% glucose (w/v). When added, kanamycin, spectinomycin, and chloramphenicol was at 25, 50 and 25 mg/l, respectively.

Metabolite Analysis by LC-MS

LC-MS data was collected on OrbiTrap Fusion High Resolution Mass Spectrometer system coupled with an Ultimate 3000 UHPLC pump (Thermo, San Jose Ca). Samples were held in the autosampler at a temperature of 10.0° C. during the analysis. 1 μL Injections of the sample were made onto a Thermo HyperSil Gold PFP HPLC column, with a 3 um particle size, 2.1 mm i.d. and 150 mm long. The column was held at a temperature of 35.0° C. The solvent system used was Solvent A "Water with 0.1% formic acid" and Solvent B "Acetonitrile with 0.1% formic". The Flow Rate was 1.000 ml/min with an Initial Solvent composition of % A=95, % B=5 held until 0.50 min, the solvent composition was then changed following a Linear Gradient until it reached % A=70.0 and % B=30.0 at 1.50 min. The solvent composition was then changed following a Linear Gradient until it reached % A=5.0 and % B=95.0 at 2.00 min This was held until 2.50 min when the solvent was returned to the initial conditions and the column was re-equilibrated until 3.00 min. The first 0.25 min of the run was diverted to waste using the divert valve, following which the column eluent flowed directly into the Heated ESI probe of the MS which was held at 325° C. and a voltage of 3500 V. Data was collected in positive ion mode over the mass range 50 to 1000 m/z at a resolution of 15.000. The other MS settings were as follows, Sheath Gas Flow Rate of 60 units, Cone Gas Flow Rate of 20 units Cone Temp was 275° C.

Designing a SAM-Selection System

L-Homocysteine and L-Cysteine Null *E. coli* Strain

To establish the SAM selection system of the invention, four features are needed. First of all, the strain is at least substantially unable to produce homocysteine from any other metabolic route except the SAM cycle (FIG. 1). Secondly, the strain is at least substantially auxotrophic for either cysteine or 2-oxobutanoate or both in order to couple the selection to cell growth. Third, there is functional expression of cystathionine-beta-synthase (EC 4.2.1.22) and cystathionine-gamma-lyase (EC 4.4.11). Lastly, the SAM-dependent methyltransferase of interest is functionally expressed.

To illustrate in *E. coli*, a deletion of the cysE gene (i.e., ΔCysE) was made. This deletion achieved two purposes: a) it resulted in a cysteine auxotrophic strain and b) it prevented de novo homocysteine biosynthesis from cysteine via the function of succinylhomoserine lyase (EC 2.5.1.48, MetB) and cystathionine-beta-lyase (EC 4.4.1.8, MetC or MalY). The resulting strain of the ΔCysE strain was named HMP174. In an alternative design, a triple deletion of cysE, metE and metH (HMP221) was made. The additional metE and metH deletion was intended to prevent the reverse enzymatic reaction of methionine to homocysteine since methionine would be added to excess during the course of laboratory evolution; however, it was later found out MetE and MetH appeared to be an irreversible step. Accordingly, in an *E. coli* host cell, deletion of MetE and/or MetH is not necessary for the growth selection coupling system.

Cystathionine-Beta-Synthase and Cystathionine-Gamma-Lyase

Active expression of cystathionin-beta-synthase and cystathionin-gamma-lyase is among the features of a functional SAM selection system. A combination of both enzymes enables the conversion of homocysteine to cysteine, hence rescuing the growth defect of HMP174 or HMP221. In this study, the gene encoding for cystathionine-beta-synthase (EC 4.2.1.22) was CYS4 from *Saccharomyces cerevisiae*; however, it may also be selected from other sources such as *Rattus norvegicus*, and *Homo sapiens*. The gene encoding for cystathionine-gamma-lyase (EC 4.4.1.1) was CYS3, also from *Saccharomyces cerevisiae* although the enzyme could alternatively be from another species, e.g., *Rattus norvegicus, Homo sapiens*, or *Bacillus subtilis*. It was observed that the effectiveness of both genes could be influenced by their expression levels, so the chosen combination was to express both genes under the synthetic J23101 promoter as an operon harbored on a SC101 origin plasmid, thereafter referred to as pHM11.

Methyltransferase

An active SAM-dependent methyltransferase was chosen so that homocysteine could be produced via the SAM-cycle enzymes. As an example, acetylserotonin methyltransferase (ASMT) from *Homo sapiens*, which catalyzes methylation of acetylserotonin to form melatonin in a SAM-dependent manner, was used. The ASMT gene was cloned onto a P15A origin plasmid and was driven under the Ptrc promoter. In addition, two additional heterologous genes, dopa decarboxylase (DDC) and serotonin acetyltransferase (AANAT) were included on the same construct so that melatonin could be synthesized directly from 5-hydroxytryptophan (5HTP). Similarly, both genes were placed under the Ptrc promoter and the final DNA vector was referred as pHM12.

Improving 5HTP to Melatonin Formation by Laboratory Evolution

5HTP-dependent growth of the HMP236 strain was observed upon transformation HMP221 with pHM11 and pHM12 in M9 with 100-mg/l of methionine and 5HTP. Initial growth of the transformed strain was weak and this indicated 5HTP to melatonin conversion was not optimal, implying that the turnover of introduced 5HTP-dependent melatonin pathway was not rapid enough to support the cellular demand for homocysteine and, hence, growth demand for cysteine. The HMP236 strain was subsequently subjected to laboratory evolution for further optimization and growth-adapted cells were isolated at the end of study.

Analysis of Evolved Strains

A total of 270 isolates were subject to analysis. The majority of the isolates were able to grow overnight at high density in M9 supplemented with 100 mg/l methionine and 5HTP at 37° c. This was in contrast to its parent strain HMP236, which was barely able to grow. In addition, most of the isolates produced melatonin from 5HTP, indicating methylation driven growth via ASMT. Strikingly, non-melatonin producing but growing cells were also identified indicating activation of native SAM-dependent methyltransferases for growth (i.e., native competing SAM sinks).

The melatonin producers could be further divided into two types. The type I producers were those that showed complete conversion of 5HTP to melatonin without any intermediates such as serotonin and acetylserotonin detected in exo-metabolites. Those cells were in contrast to type II producers where accumulation of the intermediates was observed, implying a less efficient metabolic flow from 5HTP to melatonin.

Genetic analysis was further applied. It was noted that all type I producers had accumulated mutations on the ASMT genes, G260D, T272A and A258E, respectively. Additional enzymatic analysis revealed these mutations led to improved ASMT catalytic activity from ~1-3 fold. In the type II producers, mutations were observed on the promoter regions of DDC and AANAT genes, which were required for 5HTP to serotonin and to acetylserotonin synthesis.

Based on genetic information, mutations in the cfa gene became a possible cause for the non-melatonin producer strains. Since the cfa gene encodes for a SAM-dependent fatty acid synthase and the specific mutations occurred either within the initial coding region of cfa (e.g. C5S or C5Y) or its promoter region, it was reasoned that Cfa was up-regulated to promote SAM utilization and bypass ASMT requirement for melatonin biosynthesis in the non-melatonin producing cells. It was therefore concluded Cfa is a native SAM sink in *E. coli* and can be eliminated for a more efficient SAM selection system and to improve SAM availability to the methyltransferase of interest, such as ASMT.

Example 2

Implementing SAM-Coupled 2-Oxobutanoate/Isoleucine Selection

The cystathionine-gamma-lyase (EC 4.4.1.1) converts cystathionine into L-cysteine and 2-oxobutanoate. Oxobutanoate is a precursor for isoleucine biosynthesis. Implementing a SAM-coupled isoleucine selection is beneficial since the cellular demand of isoleucine is three times larger than cysteine (276 vs 87 µmol/gm dry weight), hence achieving a three-time stronger selection.

The SAM-coupled isoleucine selection was constructed upon the SAM-coupled cysteine selection. The final background strain (HMP1072) was auxotrophic for both isoleucine/2-oxobutanoate and cysteine, hence the "SAM-IC" designation. HMP174 was the starting strain since ΔCysE was needed to prevent homocysteine biosynthesis. This was followed by ΔCfa, ΔIlvA and ΔTdcB and insertion of melatonin pathway genes (DDC, AANAT and ASMT) into the genome. The cfa deletion was implemented to eliminate the native competing SAM-dependent methyltransferase as shown in Example 1. Both ilvA and tdcB deletions were required to prevent 2-oxobutanoate synthesis from threonine. Upon transforming pHM11 into HMP1072, the final resulting strain HMP1091 was subjected to laboratory evolution in the presence of 100 mg/l of 5HTP and methionine at 37° C. in M9 medium.

Analysis of Evolved Strains

A total of 23 isolates were subjected to analysis. As shown in Table 4, nearly all had produced melatonin but only few isolates had approached the theoretical melatonin yield of 60 mg/gm dry cells. Mutation analysis indicated that mutations in the metA gene were common. This was interpreted as succinylhomoserine to 2-oxobutanoate conversion being carried out by a secondary activity of *E. coli* MetB or succinylhomoserine lyase and its precursor succinylhomoserine being directly synthesized by MetA. Thereby, reducing or eliminating MetA activity would favour SAM-IC selection. It was additionally confirmed that the HMP1233 and HMP1236 strains, which contains a metA(A28V) mutation, was non-autotrophic for methionine suggesting a reduced MetA activity.

TABLE 4

SAM-IC isolates

| Isolates | Measured melatonin yield mg/gm dry cells | Theoretical melatonin yield mg/gm dry cells | Genetic changes |
| --- | --- | --- | --- |
| HMP1218 | 45 | 60 | metF(N168D) ΔmetC metA(R34L) |
| HMP1219 | 44 | 60 | metF(N168D) metA(R34L) |
| HMP1220 | 46 | 60 | metF(N168D) metA(R34L) |
| HMP1221 | 42 | 60 | metF(N168D) ΔmetC metA(R34L) |
| HMP1222 | 30 | 60 | rpoC(K334Q) metA(R34L) |
| HMP1223 | 33 | 60 | rpoC(K334Q) metA(A28V) |
| HMP1224 | 0 | 60 | rpoC(K334Q) |
| HMP1225 | 32 | 60 | rpoC(K334Q) metA(R34L) |
| HMP1226 | 32 | 60 | rpoC(K334Q) metA(R34L) |
| HMP1227 | 32 | 60 | rpoC(K334Q) metA(R34S) |
| HMP1228 | 31 | 60 | rpoC(K334Q) metA(R34S) |
| HMP1229 | 31 | 60 | rpoC(K334Q) metA(R34S) |
| HMP1230 | 39 | 60 | metA(A28V) metC(R372C) ilvH(G21C) |
| HMP1231 | 59 | 60 | metA(A28V) metC(R372C) ilvH(G21C) |
| HMP1233 | 55 | 60 | metA(A28V) metC(R372C) ilvH(G21C) |
| HMP1234 | 33 | 60 | metA(T297K) ilvH(G14S) |
| HMP1235 | 56 | 60 | metA(A28V) ilvH(S17P) |
| HMP1236 | 59 | 60 | metA(A28V) ilvH(S17P) |
| HMP1237 | 54 | 60 | metA(A28V) ilvH(S17P) |
| HMP1238 | 22 | 60 | rpoC(K334Q) metA(S29P) |
| HMP1239 | 28 | 60 | rpoC(K334Q) metA(S29P) |
| HMP1240 | 0 | 60 | rpoC(K334Q) thrB(R235C) |
| HMP1241 | 25 | 60 | rpoC(K334Q) metA(S29P) |

Melatonin yields were measured by growing isolates in M9 with 100 mg/l 5HTP and methionine at 37° C. for 16 h.

Example 3

Melatonin Production Under SAM-Selective Conditions in Small Scale

Figure 4:
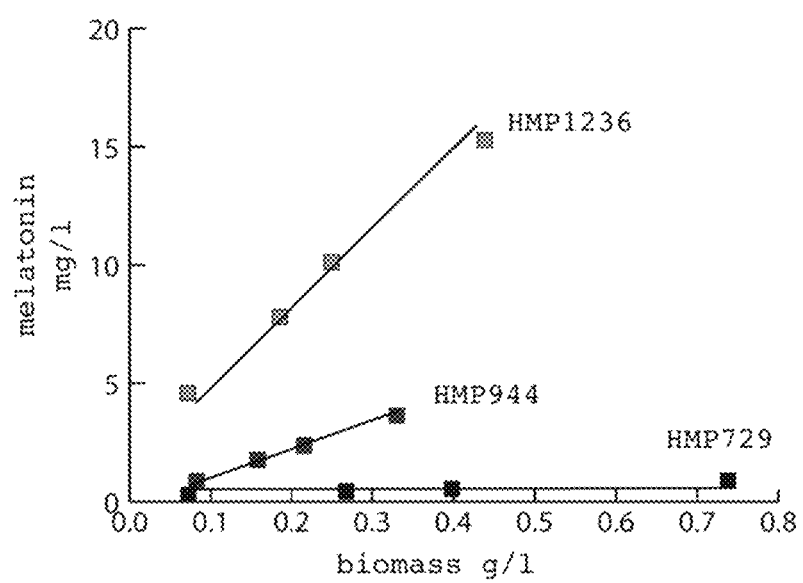
FIG. 4: Melatonin production under selective conditions in small scale. HMP729 was a non-selection strain and HMP944 and HMP1236 were grown under SAM-cysteine and SAM-IC selective conditions.

Melatonin production from 5HTP was measured under selective conditions. The three strains used were HMP729, HMP944 and HMP1236. Their genotypes are compared in Table 5. The HMP729 strain was a non-selective strain with melatonin pathway genes fully integrated into the genome. The HMP944 strain was genetically similar to HMP729 except ΔCysE to enable SAM-cysteine selection. The HMP1236 strain was SAM-IC selection enabled with additional two gene copies of ASMT and one gene copy of AANAT. Cells were characterized in small scale, in M9 medium supplemented with 100 mg/l 5HTP and 150 mg/l methionine at 37° C. As shown in FIG. 4, the results clearly showed that melatonin production was significantly improved under the selective conditions (i.e., HMP944 vs HMP729) and that the melatonin production increased as the selection pressure was increased (i.e., HMP1236 vs HMP944). Accordingly, it could be concluded that melatonin production under the selective conditions was beneficial.

TABLE 5 strain genotypes

| Isolates | Genotype |
|---|---|
| HMP729 | FolE(T198I) YnbB(V197A) ΔTnaA ΔCfa Tn7-ptrc-DDC-ptrc-AANAT-Tn7 ΔtrpR(PhhB-hsTpH(E2K, N97I, G99C)-smTpH(ΔN)-ASMT(A258E)) |
| HMP944 | HMP729 ΔCysE [CP4-6⁻ E14⁻ gshA(Y241N) relA(Q588K)][a] |
| HMP1236 | HMP729 ΔCysE ΔIlvA ΔTdcB(ASMT(A258E)) ΔYddG(AANAT(D63G)- ASMT(A258E)) [metA(A28V) ilvH(S17P) CP4-6⁻][a] |

[a]mutations acquired post laboratory evolution

Example 4

This example describes the construction of a background yeast host cell and application of the system to couple cellular growth and production of methylated products in *S. cerevisiae*, exemplified with production of caffeine from theobromine using the SAM-dependent methyltransferase caffeine synthase 1.

Strains

The laboratory strain *S. cerevisiae* CEN.PK102-5B (MATa ura3-52 his3Δ1 leu2-3/112 TRP1 MAL2-8$^C$ SUC2) (Peter Kötter, University of Frankfurt, Germany) was used as background strain for strain constructions. Marker-free gene deletions, met17Δ cho2Δ opi3Δ met2Δ set2Δ, were performed sequentially by means of CRISPR/Cas9 genome editing and verified with colony PCR. In order to obtain complete gene knockouts, upstream and downstream homologous DNA parts with overhangs to flanking regions of the genes to be deleted were amplified and used as repair templates. This strain is referred to herein as SCAH168.

An active SAM-dependent methyltransferase, caffeine synthase 1 (CCS1) from *Coffea arabica* (UniProtKB: Q8H0D3), was chosen to allow efficient L-cysteine production via the native SAM-cycle enzymes from L-methionine. This enzyme can catalyze methylation of theobromine to form caffeine in a SAM-dependent manner in *S. cerevisiae* (McKeague et al., 2016). The CCS1 was codon optimized for *S. cerevisiae* and a stop codon was added. The gene was synthesized and cloned into a tADH1-tCYC1 USER cassette (Jensen et al., 2014) of the centromeric plasmid PL_01_C7 (CEN/ARS plasmid) by means of USER cloning (Geu-flores et al., 2006). PL_01_C7 originates from pRS415 (Sikorski, R. S. & Hieter, 1989) and carries the native LEU2 gene as selection marker. Expression was driven under the native strong TDH3 promoter as well as a Kozak sequence (AAAACA) and with the native CYC1 terminator. The final DNA vector was referred as PL_01_D2. Strain SCAH182 was obtained from SCAH168 by transformation with PL_01_D2 by means of the lithium acetate/single-stranded carrier DNA/PEG protocol (Gietz and Schiest, 2007). In a similar manner, strain SCAH185 was obtained from SCAH168 by transformation with PL_01_C7 and used as control strain.

Media and Growth Conditions

All strains were maintained at 30° C. in either YPD or SC (Synthetic Dropout Medium with Supplements) (Sigma-Aldrich) lacking appropriate amino acids, and characterized in the minimal medium Delft medium (pH 5.6) (Verduyn et al., 1992). Delft medium contained (per litre): 7.5 g $(NH_4)_2SO_4$, 14.4 g $KH_2PO_4$, 0.5 g $MgSO_4.7H_2O$, 2 mL trace metals solution, 1 mL vitamin solution, and 2% glucose (w/v). The trace metal solution contained (per litre): 4.5 g $CaCl_2.2H_2O$, 4.5 g $ZnSO_4.7H_2O$, 3 g $FeSO_4.7H_2O$, 1 g $H_3BO_3$, 1 g $MnCl_2.4H_2O$, 0.4 g $Na_2MoO_4.2H_2O$, 0.3 g $CoCl_2.6H_2O$, 0.1 g $CuSO_4.5H_2O$, 0.1 g KI, 15 g EDTA. The trace metals solution was prepared by dissolving all components except EDTA in 900 ultra-pure water at pH 6. The solution was gently heated and EDTA was added. In the end, the pH was adjusted to 4, and the solution volume was adjusted to 1 L and autoclaved (121° C. for 20 minutes). This solution was stored at 4° C. The vitamin solution had (per litre): 50 mg biotin, 200 mg p-aminobenzoic acid, 1 g nicotinic acid, 1 g Ca-pantothenate, 1 g pyridoxine-HCl, 1 g thiamine-HCl, 25 g myo-inositol. Biotin was dissolved in 20 ml 0.1 M NaOH and 900 mL water is added. pH was adjusted to 6.5 with HCl and the rest of the vitamins were added. pH was re-adjusted to 6.5 just before and after adding m-inositol. The final volume was adjusted to 1 L and sterile-filtered before storage at 4° C. All media, except YPD, was supplemented with a final concentration of 1 mM choline chloride (Sigma-Aldrich).

Growth characterization of strain cell cultures was performed by measuring OD630 every 30 minute of a 96-well flat-bottom microtiter plate incubated in a microtiter plate reader BioTek ELx808 Absorbance Microplate Reader (BioTek) at 30° C./fast horizontal agitation. Similarly and in parallel, cell cultures were grown in 96-well flat-bottom microtiter plates at 30° C./300 rpm horizontal agitation for product quantification.

Product Quantification by LC-MS

For the analysis of theobromine and caffeine a HPLC system equipped with a binary pump, degasser and autosampler (Advance UHPLC system, Bruker Daltonics Inc., Fremont, Calif., USA) and a 100 mm C18 Acquity UPLC HSS T3 column (100 Å, 1.8 μm particle size, 2.1 mm i.d.; Waters, Milford, Mass., USA) with a phenomenex column filter (KrudKatcher, HPLC in-line filter, 0.5 μm×0.004 in i.d.) was used. The column oven temperature was 40° C. with an injection volume of 1 μL. The mobile phase consisted of 0.1% formic acid in MilliQ (solvent A) and 0.1% formic acid in acetonitrile (solvent B), delivered at a flow rate of 0.5 mL/min with a gradient of: 0.0-0.2 min: 10% B, 0.2-1.0 min: 10% B→70% B, 1.0-1.3 min: 70% B, 1.3-1.35 min: 70% B→10% B, 1.35-2.5 min: 10% B.

As detector a triple quadrupole mass spectrometer (EVOQ Elite, Bruker Daltonics Inc., Fremont, Calif., USA) with electrospray ionization in positive mode with multiple reaction monitoring (MRM) was used. The instrument settings were as followed: spray voltage: 4.5 kV, cone temperature: 350° C., cone gas flow 20, probe gas flow: 50, nebulizer gas flow: 50, heated probe temperature: 300° C., exhaust gas: on, collision gas pressure: 1.5 mTorr. The MRM scan time was set to 100 ms with standard resolution for all transitions. The collision energy (CE) was optimized for each transition. The quantifiers used were m/z 195.1→138 (CE: 15 eV) and m/z 181.0→110 (CE: 20 eV) for caffeine (retention time: 1.2 min) and theobromine (retention time: 0.9 min), respectively. The qualifiers for caffeine were m/z 195.1→123 (CE: 28 eV) and m/z 195.1→110 (CE: 22 eV) and for theobromine m/z 181.0→138 (CE: 15 eV).

Stock solutions were prepared in MilliQ-water and the calibration standard was prepared by appropriate dilutions in media and MilliQ-water for caffeine and theobromine analysis, respectively.

Culture broth from the 96-well flat-bottom microtiter plate was filtered by centrifugation using filter plates (96-well, for multiplexing, AcroPrep Advance from VWR) and the flow-through was injected undiluted and diluted 20 times with MilliQ-water for caffeine and theobromine analysis. Titers were corrected for background caffeine initially present in the medium with theobromine (control media).

Caffeine Production Under SAM-Selective Conditions in Small Scale

Growth characterization and caffeine production was measured under selective conditions using strains SCAH182 and SCAH185.

Prior to inoculation for characterization, cells were grown from OD600 ~0.01 to ~2.0 (measured on a spectrophotometer, 1 cm pathlength) in SC medium lacking leucine supplied with 1 mM choline chloride, 2 ml was harvested and washed twice in sterile water, and re-incubated in Delft medium (final volume of 1.5× the harvested volume) (prepared as described above) supplied with histidine, uracil and 1 mM choline chloride for another 27 hours incubation at 30° C./250 rpm for sulphur amino acid starvation. After starvation, cells were characterized, as described above, in small scale in 96-well flat-bottom microtiter plates in 150 μL Delft medium (preparation as described above) supplemented with histidine, uracil, 1 mM choline chloride and 1 mM (0.15 g/L) L-methionine as well as in the presence or absence of the substrate 1 mM theobromine at 30° C.

Figure 5:
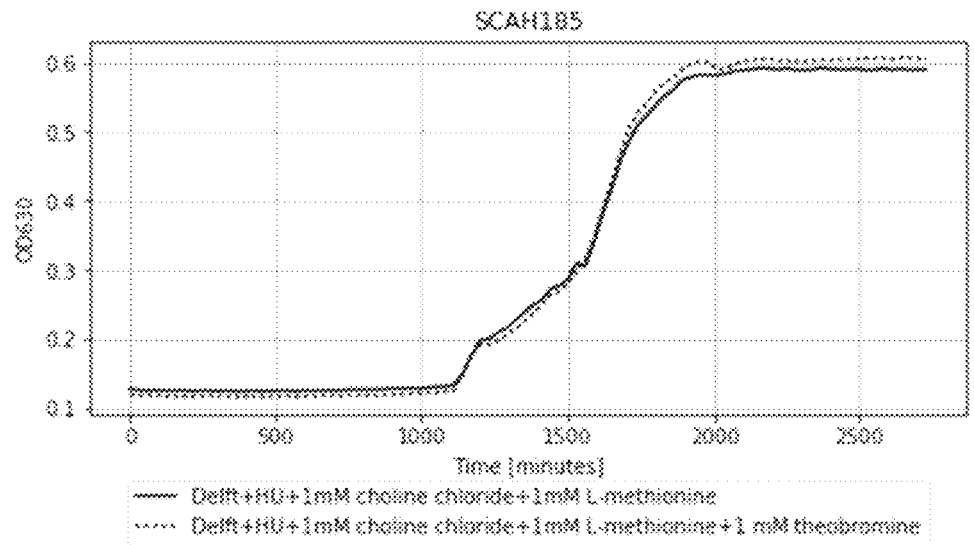
FIG. 5: Growth of SCAH182 (B, C, D) and SCAH185 (A, C, D) in selective conditions in Delft medium supplied with histidine and uracil (HU), 1 mM choline chloride and 1 mM L-methionine with (A, B, D) and without (A, B, C) 1 mM theobromine. Growth curves represents an average of three replicates (N=3) grown in a 96-well flat-bottom microtiter plate. Measurements were taken in a BioTek ELx808 Absorbance Microplate Reader (BioTek)s every 30 minute.
Figure 5:
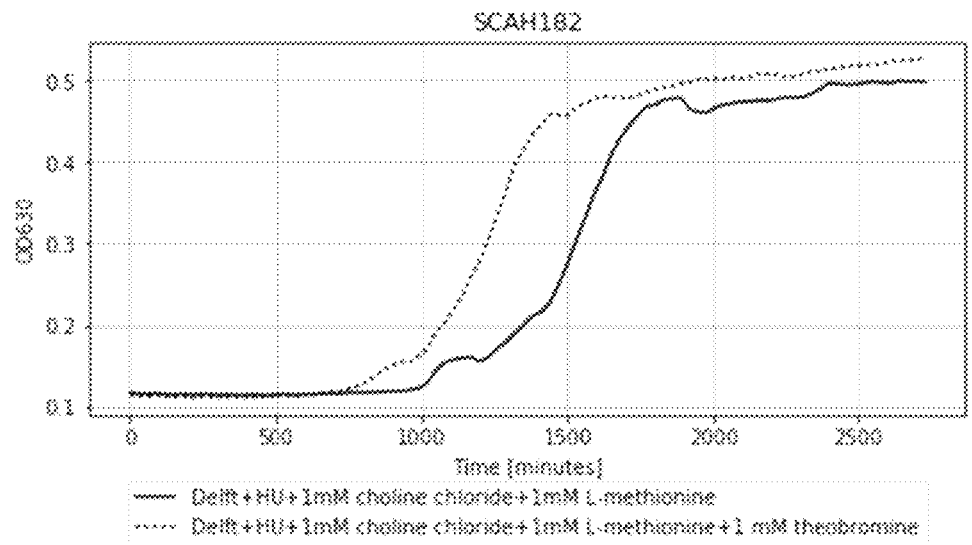
Figure 5:
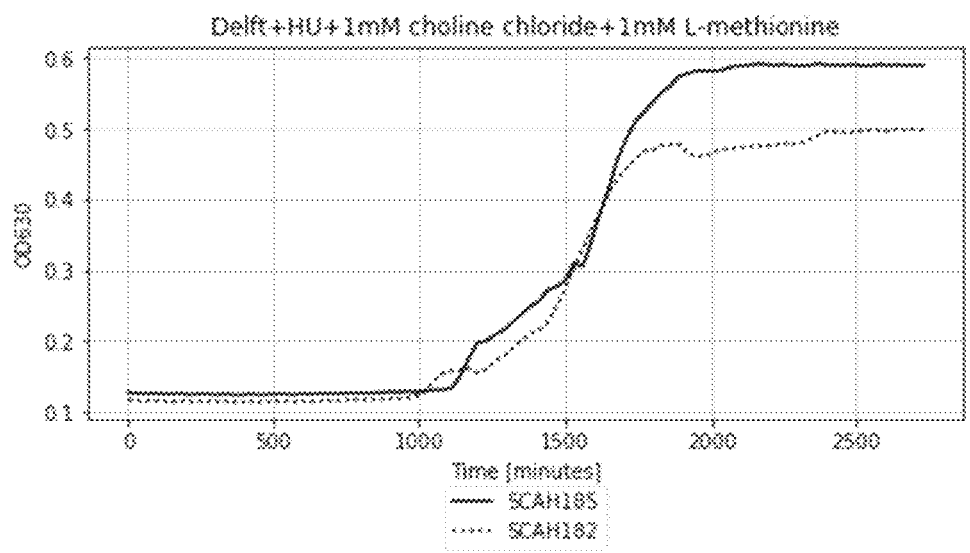
Figure 5:
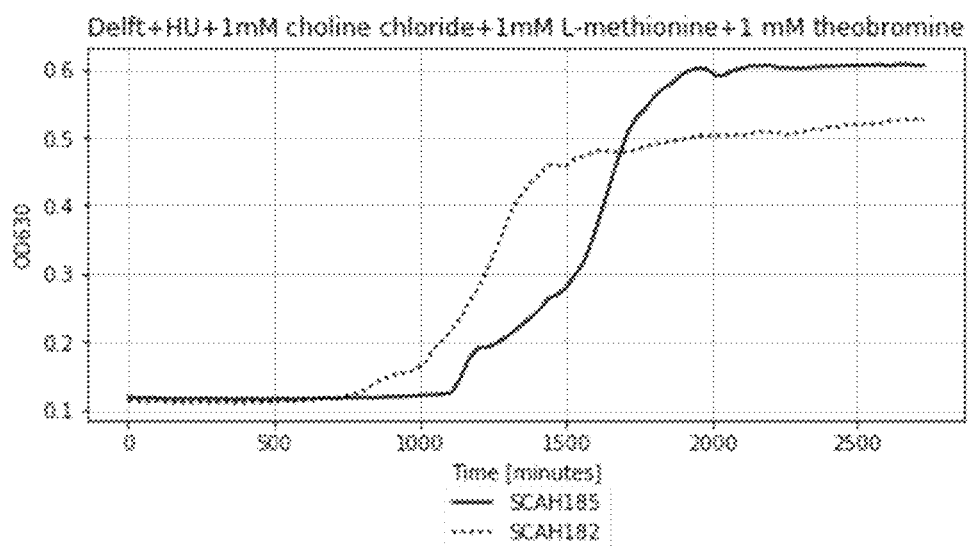

SCAH185 and SCAH182 were both still able to grow in the presence of 1 mM L-methionine (FIG. 5). However, the growth rate was reduced and the lag time increased as compared to the native strain (data not shown). The genes for the native methyltransferases CHO2, OPI3 and SET2 had been deleted from both strains, so this growth was possibly due to active expression of other native SAM-dependent methyltransferases. Similar experiments were performed with *S. cerevisiae* strains having the deletions met17Δ cho2Δ opi3Δ met6Δ set2Δ set1Δ, met17Δ cho2Δ opi3Δ met6Δ set2Δ or met17Δ cho2Δ opi3Δ met6Δ set2Δ set1Δ dot1Δ (with SET1, SET2, DOT1 representing other native methyltransferases as well as MET6), yielding similar results (data not shown).

As shown in FIG. 5, the CCS1-bearing strain, SCAH182, displayed a pronounced growth advantage when the substrate theobromine was supplemented in the media. This result was in contrast to the SCAH185 cells, a non-CCS1-bearing strain, where addition of theobromine offered no growth advantage. Moreover, caffeine production (average titer of 23.7±2.6 mg/L at the end of ~46 hs cultivation when OD630 was 0.57 measured directly on BioTek ELx808 Absorbance Microplate Reader (BioTek) (N=3)) was only detected for SCAH182 under the selective conditions when theobromine was added. Overall, these results concluded that the growth advantage of SCAH182 cells under theobromine-supplemented conditions had in fact benefited from L-cysteine formation via homocysteine of the SAM cycle, and hence achieved a functional methylation-dependent growth selection.

LIST OF REFERENCES

Duchin et al., Epigenetics & Chromatin 2015; 8:56
Frederick et al., *Chemical Composition of Escherichia coli*, Chapter 3, *Escherichia coli and Salmonella: cellular and molecular biology*, $2^{nd}$ edition, Vol 1. (1996) American Society of Microbiology Press.
Struck et al., Chembiochem. 2012 Dec. 21; 13(18):2642-55
Tengg et al., Journal of Molecular Catalysis B: Enzymatic 2012, 84:2-8
Lyon and Jakoby, J Biol Chem 1982; 257:7531-7535
Attieh et al., Plant Mol Biol 2002, 50:511-521
Bennett et al., Nat Chem Biol 2009, 5:593-599
Ye et al., Molecular Cell 2017, 66:1-14
Sadhu et al., Molecular Biology of the Cell 2014, 25:1653-65
McKeague et al., Metab. Eng. 38, 191-203 (2016)
Gietz and Schiest, Nat. Protoc. 2, 31-34 (2007)
Geu-flores et al., Nucleic Acids Res. 2007 April; 35(7): e55
Verduyn et al., Yeast 8, 501-17 (1992)
Sikorski and Hieter, Genetics 122(1), 19-27 (1989)
Jensen et al., *FEMS Yeast Res.* 14, 238-248 (2014)
WO 2016/082252 (Metabolic Explorer)
U.S. Pat. No. 7,745,195 (Metabolic Explorer)
WO 2013/127915 A1 (Danmarks Tekniske Universitet)
WO 2015/032911 A1 (Danmarks Tekniske Universitet)
US 2014/134689 AA (University of California)

The invention claimed is:

1. A genetically modified *E. coli* cell comprising a s-adenosyl methionine- (SAM) -dependent methyltransferase, a heterologous cystathionine-beta-synthase selected from *Saccharomyces cerevisiae, Streptomyces coelicolor, Streptomyces griseus, Clostridium acetobutylicum, Arabidopsis thaliana* and *Homo sapiens* cystathionine-beta-synthase, and a heterologous cystathionine-gamma-lyase selected from *Saccharomyces cerevisiae, Clostridium glutamicum, Streptomyces coelicolor, Streptomyces griseus, Bacillus subtilis* and *Homo sapiens* cystathionine gamma-lyase, and
(a) a downregulation or deletion of cysE;
(b) a downregulation or deletion of cysK and cysM;
(c) a downregulation or deletion of cysE and ilvA;
(d) a downregulation or deletion of cysE and tdcB;
(e) a downregulation or deletion of cysE, ilvA and tdcB;
(f) a downregulation or deletion of cysE, ilvA, tdcB, and metA;
(g) a downregulation or deletion of cysE, ilvA, tdcB, and metB;
(h) a downregulation or deletion of metA, ilvA and tdcB;
(i) a downregulation or deletion of metB, ilvA and tdcB;
(j) a downregulation or deletion of metC, malY, ilvA and tdcB;
(k) a downregulation or deletion of metC, malY, ilvA, tdcB and metA;
(l) a downregulation or deletion of metC, malY, ilvA, tdcB and metB; or
(m) any one of (a) to (l), further comprising a downregulation or deletion of cfa,
wherein, in (a) to (m), the downregulation of a gene reduces the level of enzyme encoded by the gene by at least 95%.

2. The genetically modified cell of claim 1, wherein the SAM-dependent methyltransferase is selected from the group consisting of an O-methyltransferase, a C-methyltransferase, an N-methyltransferase and an S-methyltransferase.

3. A composition comprising a plurality of the genetically modified *E. coli* cell of claim 1.

4. The composition of claim 3, comprising a culture medium comprising methionine, at least one substrate or substrate precursor of the SAM-dependent methyltransferase, and a carbon source.

5. A method of preparing a genetically modified *E. coli* cell according to claim 1, said genetically modified *E. coli* cell is growth-dependent on a metabolite selected from cysteine, 2-oxobutanoate, isoleucine, and a combination of any thereof, comprising the steps of
(i) transforming an *E. coli* cell with a nucleic acid encoding a SAM-dependent methyltransferase;
(ii) transforming the *E. coli* cell with nucleic acids encoding a cystathionine-beta-synthase and a cystathionine-gamma-lyase; and
(iii) downregulating or deleting the gene or genes according to any one of (a) to (m), wherein, in (a) to (m), the downregulation of a gene reduces the level of enzyme encoded by the gene by at least 95%,
wherein steps (i) to (iii) are performed in any order.

6. A method of evolving the SAM-dependent methyltransferase activity of an *E. coli* cell, comprising cultivating the genetically modified cell of claim 1 in a medium comprising an abundance of methionine, at least one substrate or substrate precursor of the SAM-dependent methyltransferase, and a carbon source.

7. A method of preparing an *E. coli* cell having an improved SAM-dependent methyltransferase activity, comprising the steps of:
(a) culturing a plurality of the genetically modified *E. coli* cell of claim 1 in a medium comprising an abundance of methionine, at least one substrate or substrate precursor of the SAM-dependent methyltransferase, and a carbon source; and
(b) selecting any *E. coli* cell having an increased growth rate as compared to the genetically modified bacterial cell prior to step (a) as a cell having an improved SAM-dependent methyltransferase activity.

8. A genetically modified *E. coli* cell prepared by the method of claim 5.

9. A method of producing a methylated product from a substrate of a SAM-dependent methyltransferase, the method comprising the steps of:
(a) culturing a plurality of the genetically modified *E. coli* cell of claim 1 in a medium comprising an abundance of methionine, at least one substrate or substrate precursor of the SAM-dependent methyltransferase, and a carbon source;
(b) selecting any *E. coli* cell having an increased growth rate as compared to the genetically modified *E. coli* cell prior to step (a) as a cell having an improved SAM-dependent methyltransferase activity;
(c) producing the methylated product by fermenting an *E. coli* cell selected in step (b) in a medium comprising methionine, the substrate or substrate precursor of the SAM-dependent methyltransferase, and a carbon source; and (d) optionally, retrieving the methylated product from the E. coli cell or fermentation medium.

10. The genetically modified *E. coli* cell of claim 1, wherein the heterologous cystathionine-beta-synthase is *S. cerevisiae* cystathionine-beta-synthase, and the heterologous cystathionine-gamma-lyase is *S. cerevisiae* cystathionine-gamma-lyase.

11. The genetically modified *E. coli* cell of claim 8, wherein the heterologous cystathionine-beta-synthase and the heterologous cystathionine-gamma-lyase are *S. cerevisiae* cystathionine-beta-synthase and *S. cerevisiae* cystathionine-gamma-lyase, respectively.

12. The genetically modified *E. coli* cell of claim 10, comprising a downregulation or deletion of cysE.

13. The genetically modified *E. coli* cell of claim 11, comprising a downregulation or deletion of cysE.

* * * * *